United States Patent
Kataoka et al.

(10) Patent No.: US 11,990,207 B2
(45) Date of Patent: May 21, 2024

(54) METHOD OF IDENTIFICATION, NON-TRANSITORY COMPUTER READABLE RECORDING MEDIUM, AND IDENTIFICATION APPARATUS

(71) Applicant: FUJITSU LIMITED, Kawasaki (JP)

(72) Inventors: Masahiro Kataoka, Kamakura (JP); Kota Natsume, Ota (JP); Satoshi Kitadate, Chiba (JP)

(73) Assignee: FUJITSU LIMITED, Kawasaki (JP)

( * ) Notice: Subject to any disclaimer, the term of this patent is extended or adjusted under 35 U.S.C. 154(b) by 1151 days.

(21) Appl. No.: 16/774,071

(22) Filed: Jan. 28, 2020

(65) Prior Publication Data
US 2020/0279615 A1    Sep. 3, 2020

(30) Foreign Application Priority Data
Feb. 28, 2019  (JP) .................. 2019-036298

(51) Int. Cl.
| G16B 30/00 | (2019.01) |
| G06F 16/13 | (2019.01) |
| G06F 16/174 | (2019.01) |
| G16B 15/00 | (2019.01) |
| G16B 50/50 | (2019.01) |

(52) U.S. Cl.
CPC ............ G16B 30/00 (2019.02); G06F 16/13 (2019.01); G06F 16/1744 (2019.01); G16B 15/00 (2019.02); G16B 50/50 (2019.02)

(58) Field of Classification Search
CPC ..... G16B 30/00; G16B 50/50; G06F 16/1744; G06F 16/13
See application file for complete search history.

(56) References Cited

FOREIGN PATENT DOCUMENTS

| JP | 2003-256433 A | 9/2003 |
| JP | 2004-280614 A | 10/2004 |

*Primary Examiner* — Russell S Negin
*Assistant Examiner* — Guozhen Liu
(74) *Attorney, Agent, or Firm* — Fujitsu Intellectual Property Center

(57) ABSTRACT

An identification apparatus acquires a protein file in which a plurality of proteins including a plurality of amino acids are arranged. The identification apparatus identifies a plurality of primary structure candidates with any position included in the protein file as a starting position. The identification apparatus identifies one primary structure among the primary structure candidates based on a combination of a primary structure and each amino acid and a primary structure table, where the each amino acid is positioned at an end of the primary structure and the primary structure table associates a primary structure and a cooccurrence rate of a certain amino acid combination positioned at an end of the primary structure.

8 Claims, 25 Drawing Sheets

FIG.6

|  | 4(0100) | 5(0101) | 6(0110) | 7(0111) |
|---|---|---|---|---|
| 0(0000) | UUU | CUU | AUU | GUU |
| 1(0001) | UUC | CUC | AUC | GUC |
| 2(0010) | UUA | CUA | AUA | GUA |
| 3(0011) | UUG | CUG | AUG | GUG |
| 4(0100) | UCU | CCU | ACU | GCU |
| 5(0101) | UCC | CCC | ACC | GCC |
| 6(0110) | UCA | CCA | ACA | GCA |
| 7(0111) | UCG | CCG | ACG | GCG |
| 8(1000) | UAU | CAU | AAU | GAU |
| 9(1001) | UAC | CAC | AAC | GAC |
| A(1010) | UAA | CAA | AAA | GAA |
| B(1011) | UAG | CAG | AAG | GAG |
| C(1100) | UGU | CGU | AGU | GGU |
| D(1101) | UGC | CGC | AGC | GGC |
| E(1110) | UGA | CGA | AGA | GGA |
| F(1111) | UGG | CGG | AGG | GGG |

| PROTEIN INFORMATION | | | AMINO ACID CODE SEQUENCE | CODON CODE SEQUENCE |
|---|---|---|---|---|
| CODE | GROUP | NAME | | |
| 8000h | COLLA-GEN | TYPE I COLLAGEN | 02h46h59h⋯⋯⋯03h | 02h63h78h⋯⋯⋯03h |
| 8001h | COLLA-GEN | TYPE II COLLAGEN | 02h52h4Eh⋯⋯⋯03h | 02h52h79h⋯⋯⋯03h |
| 8002h | COLLA-GEN | TYPE III COLLAGEN | 02h43h⋯⋯⋯03h | 02h66h⋯⋯⋯03h |
| 8003h | COLLA-GEN | TYPE IV COLLAGEN | ... | ... |
| 8004h | COLLA-GEN | TYPE V COLLAGEN | ... | ... |
| 8005h | COLLA-GEN | TYPE VI COLLAGEN | ... | ... |
| 8006h | COLLA-GEN | TYPE VII COLLAGEN | ... | ... |
| 8007h | COLLA-GEN | TYPE VIII COLLAGEN | ... | ... |
| 8008h | COLLA-GEN | TYPE IX COLLAGEN | ... | ... |
| 8009h | COLLA-GEN | TYPE X COLLAGEN | ... | ... |
| 800Ah | COLLA-GEN | TYPE XI COLLAGEN | ... | ... |
| 800Bh | COLLA-GEN | TYPE XV COLLAGEN | ... | ... |
| 800Ch | COLLA-GEN | TYPE XVII COLLAGEN | ... | ... |
| 800Dh | COLLA-GEN | TYPE XVIII COLLAGEN | ... | ... |
| 800Eh | KERATIN | ACTIN FILAMENT | ... | ... |
| 800Fh | KERATIN | KERATIN FILAMENT | ... | ... |
| 8010h | KERATIN | NEUROFILAMENT | ... | ... |
| 8011h | KERATIN | DESMIN | ... | ... |
| 8012h | KERATIN | VIMENTIN | ... | ... |
| 8013h | KERATIN | α TUBULIN | ... | ... |
| 8014h | KERATIN | β TUBULIN | ... | ... |
| 8015h | KERATIN | γ TUBULIN | ... | ... |
| 8016h | KERATIN | δ TUBULIN | ... | ... |

| PROTEIN INFORMATION | | | COOCCURRING PROTEIN INFORMATION | | | | | | |
|---|---|---|---|---|---|---|---|---|---|
| CODE | GROUP | NAME | CODE | COOCCURRENCE RATE | CODE | COOCCURRENCE RATE | CODE | COOCCURRENCE RATE | ... |
| 8000h | COLLAGEN | TYPE I COLLAGEN | 8028h | 78% | 8132h | 63% | 80F5h | 51% | ... |
| 8001h | COLLAGEN | TYPE II COLLAGEN | 81E3h | 81% | 8021h | 71% | 8241h | 57% | ... |
| 8002h | COLLAGEN | TYPE III COLLAGEN | | | | ⋮ | | | |

| PRIMARY STRUCTURE INFORMATION | | | PROTEIN CODE SEQUENCE |
|---|---|---|---|
| CODE | GROUP | NAME | |
| F00000h | G1 | α PRIMARY SEQUENCE | 02h8028h·················03h |
| F00001h | G1 | β PRIMARY SEQUENCE | 02h80F5h············03h |
| F00002h | G1 | γ PRIMARY SEQUENCE | 02h81E3h················03h |
| ... | ... | ... | ... |

FIG.20

| AMINO ACID COMBINATION INFORMATION | | COOCCURRING PRIMARY STRUCTURE INFORMATION | | | | | | |
|---|---|---|---|---|---|---|---|---|
| CODE | NAME | CODE | COOCCURRENCE RATE | CODE | COOCCURRENCE RATE | CODE | COOCCURRENCE RATE | ... |
| 47h41h50h | GLYCINE·ALANINE·LEUCINE | F08028h | 78% | F08132h | 63% | F080F5h | 51% | ... |
| 46h43h | SERINE·LEUCINE | F081E3h | 81% | F08021h | 71% | F08241h | 57% | ... |
| 46h47h | SERINE·ALANINE | ... | ... | ... | ... | ... | ... | ... |

250b

FIG.24
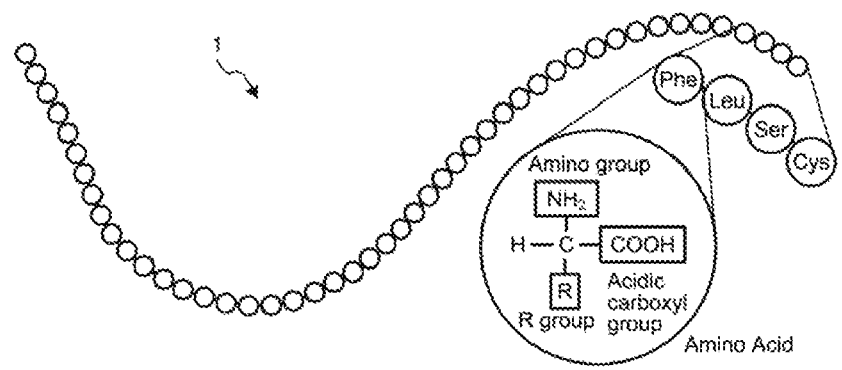
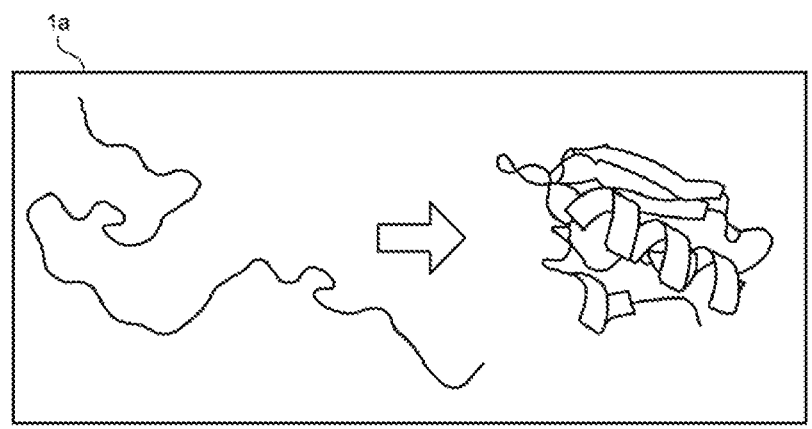
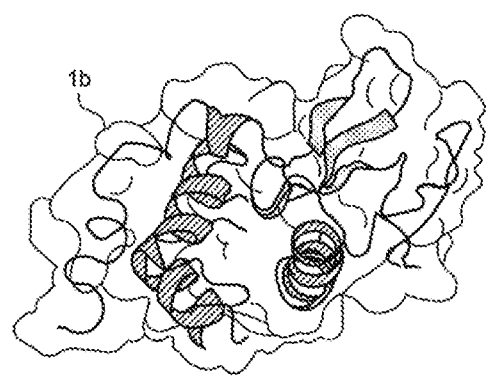

FIG.25

| AMINO ACID | | | BASE (THREE-BASE SEQUENCE: CODON) | | | |
|---|---|---|---|---|---|---|
| NAME | ABBREVIATION | SYMBOL | | | | |
| ALANINE | Ala | A | GCU | GCC | GCA | GCG |
| CYSTEINE | Cys | C | UGU | UGC | | |
| ASPARTIC ACID | Asp | D | GAU | GAC | | |
| GLUTAMIC ACID | Glu | E | | | GAA | GAG |
| PHENYLALANINE | Phe | F | UUU | UUC | | |
| GLYCINE | Gly | G | GGU | GGC | GGA | GGG |
| HISTIDINE | His | H | CAU | CAC | | |
| ISOLEUCINE | Ile | I | AUU | AUC | AUA | |
| LYSINE | Lys | K | | | AAA | AAG |
| LEUCINE | Leu | L | | | UUA | UUG |
| | | | CUU | CUC | CUA | CUG |
| METHIONINE (INITIATION) | Met | M | | | | AUG |
| ASPARAGINE | Asn | N | AAU | AAC | | |
| PROLINE | Pro | P | CCU | CCC | CCA | CCG |
| GLUTAMINE | Gln | Q | | | CAA | CAG |
| ARGININE | Arg | R | CGU | CGC | CGA | CGG |
| | | | | | AGA | AGG |
| SERINE | Ser | S | UCU | UCC | UCA | UCG |
| | | | AGU | AGC | | |
| THREONINE | Thr | T | ACU | ACC | ACA | ACG |
| VALIN | Val | V | GUU | GUC | GUA | GUG |
| TRYPTOPHAN | Trp | W | | | | UGG |
| TYROSINE | Tyr | Y | UAU | UAC | | |
| (TERMINATION) | | | | | UAA | UAG |
| (TERMINATION) | | | | | UGA | |
| UNDETERMINED AMINO ACID | Xxx | X | | | | |
| EITHER GLUTAMIC ACID OR GLUTAMINE) | Glx | Z | | | | |

METHOD OF IDENTIFICATION, NON-TRANSITORY COMPUTER READABLE RECORDING MEDIUM, AND IDENTIFICATION APPARATUS

CROSS-REFERENCE TO RELATED APPLICATION(S)

This application is based upon and claims the benefit of priority of the prior Japanese Patent Application No. 2019-036298, filed on Feb. 28, 2019, the entire contents of which are incorporated herein by reference.

FIELD

The embodiments discussed herein are related to a method of identification and the like.

BACKGROUND

In recent years, genomes included in deoxyribonucleic acid (DNA) and ribonucleic acid (RNA) of living bodies have been analyzed to predict the influence of new viruses and to develop vaccines and the like. Researches are being conducted that detect gene abnormalities of mutations (point mutations) such as cancer and gene mutations or diagnose the risk of occurrence of diseases based on genomes.

FIG. 24 is a diagram for illustrating a genome. This genome 1 is genetic information in which a plurality of amino acids are coupled to each other. The amino acid is determined by a plurality of bases, or a codon. The genome 1 includes a protein 1a. The protein 1a includes a plurality of 20 kinds of amino acids coupled to each other, in which they are coupled to each other like a chain. The structure of the protein 1a includes a primary structure, a secondary structure, and a tertiary (a higher order) structure. A protein 1b is a protein with the higher order structure.

DNA and RNA have four kinds of bases, which are represented by the symbols "A," "G," "C," and "T," or "U." A three-base sequence as a mass determines 20 kinds of amino acids. Each amino acid is represented by the symbols "A" to "Y." FIG. 25 is a diagram of a relation among the amino acid, the base, and the codon. A mass of the three-base sequence is called a "codon." An arrangement of bases determines a codon, and the determined codon determines an amino acid.

As illustrated in FIG. 25, a plurality of types of codons are associated with one amino acid. Consequently, when the codon is determined, the amino acid is determined, but even when the amino acid is determined, the codon is not uniquely identified. The amino acid "alanine (Ala)" is associated with the codon "GCU," "GCC," "GCA," or "GCG," for example.

As a technology that searches a genome for certain information, there is a conventional technology that compares base or amino acid sequences by creating an index by the encoding of oligo sequences and searches a database for a specific oligo sequence. Conventional technologies are described in Japanese Laid-open Patent Publication No. 2003-256433 and Japanese Laid-open Patent Publication No. 2004-280614, for example.

SUMMARY

According to an aspect of an embodiment, a method of identification includes acquiring a protein file in which a plurality of proteins including a plurality of amino acids are arranged, using a processor; identifying a plurality of primary structure candidates with any position included in the protein file as a starting position, using the processor; and identifying one primary structure among the primary structure candidates based on a combination of a primary structure and each amino acid and a primary structure table, where the each amino acid is positioned at an end of the primary structure and the primary structure table associates a primary structure and a cooccurrence rate of a certain amino acid combination positioned at an end of the primary structure, using the processor.

The object and advantages of the invention will be realized and attained by means of the elements and combinations particularly pointed out in the claims.

It is to be understood that both the foregoing general description and the following detailed description are exemplary and explanatory and are not restrictive of the invention, as claimed.

BRIEF DESCRIPTION OF DRAWINGS

FIG. 6 is a diagram of an exemplary data structure of a conversion table;

FIG. 8 is a diagram of an exemplary data structure of a protein dictionary;

FIG. 9 is a diagram of an exemplary data structure of a protein hidden Markov model (HMM);

FIG. 11 is a diagram for illustrating exemplary processing to hash the codon transposition index;

FIG. 12 is a diagram for illustrating exemplary processing to identify a protein included in a codon compression file by a cooccurrence totalization unit;

FIG. 13 is a diagram for illustrating processing to reconstruct the hashed bitmap;

FIG. 19 is a diagram of an exemplary data structure of a primary structure dictionary;

FIG. 20 is a diagram of an exemplary data structure of a primary structure HMM;

FIG. 24 is a diagram for illustrating a genome; and

FIG. 25 is a diagram of a relation among an amino acid, a base, and a codon.

DESCRIPTION OF EMBODIMENTS

However, the conventional technologies described above have a problem in that the primary structure of proteins included in the genome is not able to be identified.

Information on the genome is various such as information by base, information by codon, or information by amino acid, for example. Conventional technologies are not able to convert the information by amino acid into the information by codon. Given these circumstances, dictionary information or the like with which information on the primary structure of proteins is associated may be created by base, codon, and amino acid, and a comparison between the genome and dictionary information may be performed; an enormous amount of data of the dictionary information reduces the speed of identifying the primary structure.

Preferred embodiments of the present invention will be explained with reference to accompanying drawings. These examples do not limit the present invention.

[a] First Example

FIG. 1 to FIG. 4 are diagrams for illustrating processing by an identification apparatus according to a first example. The following first describes FIG. 1. A base file 150a is a file holding information in which a plurality of bases are arranged. DNA and RNA have four kinds of bases, which are represented by the symbols "A," "G," "C," and "T," or "U."

A first encoding unit 160b of the identification apparatus generates a codon compression file 150c and a codon transposition index 150d from the base file 150a based on a conversion table 150b.

The conversion table 150b is a table associating a codon and a codon code with each other. A mass of a three-base sequence is called a "codon."

The first encoding unit 160b extracts bases in groups of three from the base file 150a and compares the extracted bases and the conversion table 150b with each other to identify a code corresponding to three bases (a codon) and converts the three bases (the codon) into the code. The first encoding unit 160b repeatedly executes the processing to generate the codon compression file 150c. The codon compression file 150c is information in which codes by codon are arranged. In the first example, bases (a codon) before encoding are represented within parentheses next to a code for the sake of convenience. The codon "AUG" is converted into a code "63h," for example, in which the converted code is denoted by "(AUG)63h." The letter "h" indicates that it is a hexadecimal number.

When generating the codon compression file 150c, the first encoding unit 160b generates the codon transposition index 150d. The codon transposition index 150d is information associating an offset from the top of the codon compression file 150c and a codon type (the codon code) with each other.

Figure 1:
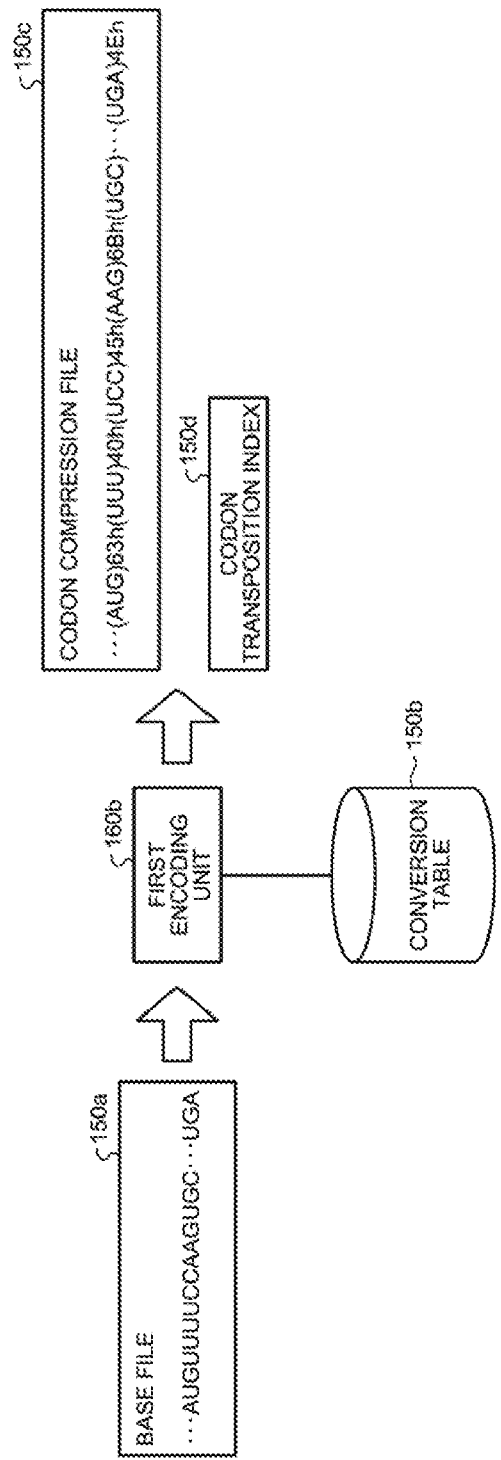
FIG. 1 is a diagram (1) for illustrating processing by an identification apparatus according to a first example.
Figure 2:
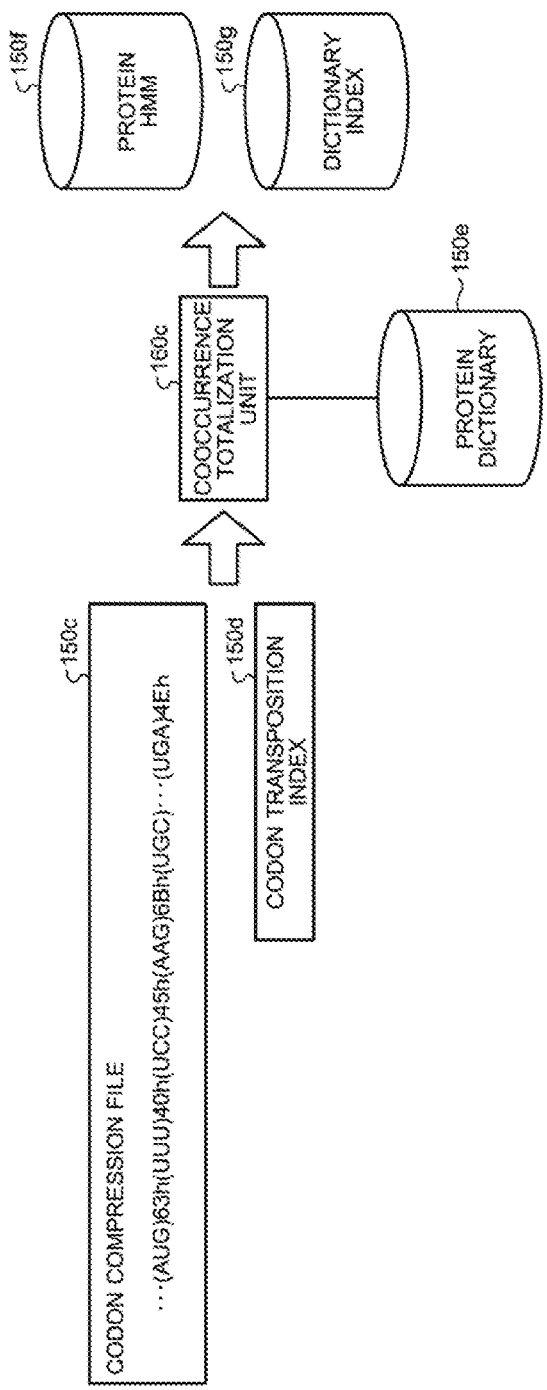
FIG. 2 is a diagram (2) for illustrating the processing by the identification apparatus according to the first example.

The following describes FIG. 2. A cooccurrence totalization unit 160c of the identification apparatus generates a protein hidden Markov model (HMM) 150f and a dictionary index 150g based on the codon compression file 150c, the codon transposition index 150d, and a protein dictionary 150e.

The protein dictionary 150e is information associating a protein code and a codon code sequence with each other. The codon code sequence is information in which a plurality of codon codes are arranged combination of codons (codon codes) varies in accordance with the type of the protein, and the number of codons corresponding to the protein varies.

The cooccurrence totalization unit 160c identifies a codon combination included in the codon compression file 150c based on the codon transposition index 150d. The cooccurrence totalization unit 160c repeatedly executes processing to compare the codon combination. (the codon code sequence) and the codon code sequence of the protein dictionary 150e with each other to identify protein codes included in the codon compression file 150c.

The cooccurrence totalization unit 160c, in the process of repeatedly executing the above processing, sets a "break" of the codon code sequence corresponding to each protein included in the codon compression file 150c in the dictionary index 150g. In a codon code sequence "02h63h78h••03h02h52h79h•03h," for example, the codon code sequence "02h63h78h••03h" is a codon code sequence corresponding to a protein code "8000h," whereas the codon sequence "02h52h79h•03h" is a codon sequence corresponding to a protein code "8001h." In this case, the gap between the codon code sequences "02h63h78h••03h" and "02h52h79h••03h" is the "break." In the dictionary index 150g, each break is indicated by the offset from the top of the codon compression file 150c. In the first example, the break is indicated by the offset of a top code of a following codon code sequence as an example. In the above example, the offset of the top code <02h> of the following "02h52h79h••03h" is the offset of the break.

In the process in which the cooccurrence totalization unit 160c performs the above processing, a codon code sequence from a certain offset of the codon compression file 150c may match a plurality of codon code sequences having different lengths included in the protein dictionary 150e.

Figure 3:
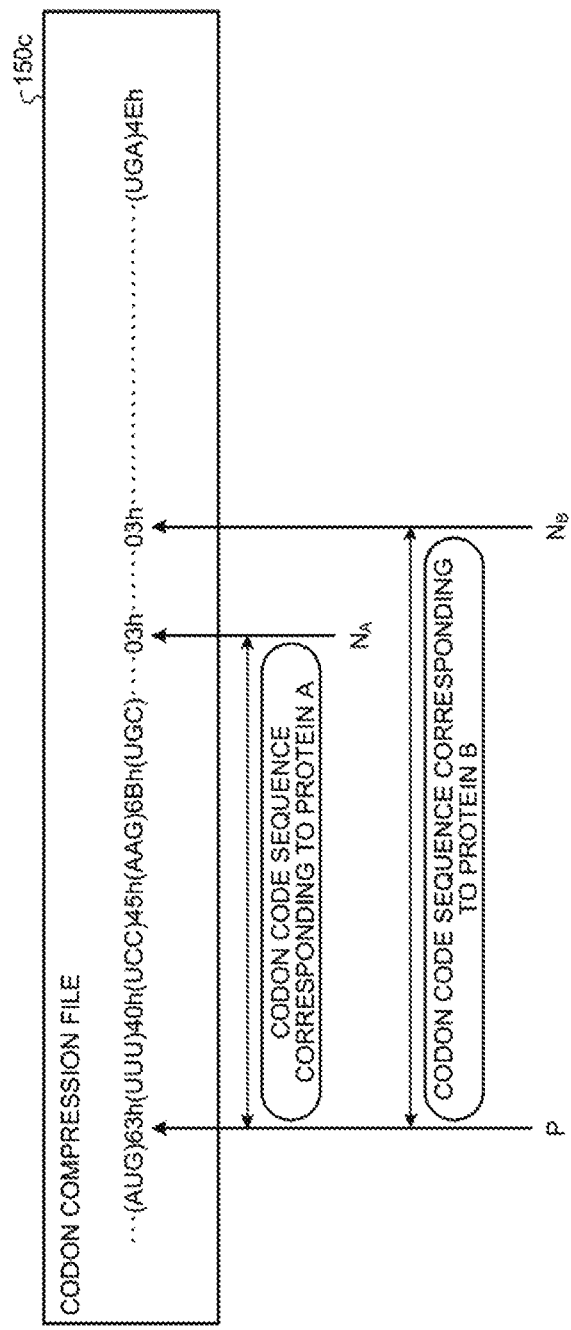
FIG. 3 is a diagram (3) for illustrating the processing by the identification apparatus according to the first example.

As illustrated in FIG. 3, for example, a codon code sequence from an offset P of a certain break of the codon compression file 150c to an offset may correspond to the code of a protein A, whereas a codon code sequence from the offset P to an offset $N_3$ may match the code of a protein B.

In this case, the cooccurrence totalization unit 160c sets the codon code of offsets P to $P+N_A$ as the code of the protein A, sets an offset. $P+N_A+1$ as a break, and repeatedly executes the above processing. The cooccurrence totalization unit 160c sets the codon code of offsets P to $P+N_B$ as the code of the protein B, sets an offset $P+N_B+1$ as a break, and repeatedly executes the above processing.

The cooccurrence totalization unit 160c repeatedly executes the above process to totalize the type of a protein code following a certain protein code and to calculate a cooccurrence rate with the certain protein code. It is assumed that the codon code sequence of the protein A has appeared $M_A$ times in the codon compression file 150c, for example. When the codon code sequence of the protein. B among various kinds of proteins following the codon code sequence of the protein A has appeared $L_B$ times, the cooccurrence rate of the code of the protein A and the code of the protein B is "$L_B/M_A/100$." The cooccurrence totalization unit 160c repeatedly executes the processing to calculate the cooccurrence rate for each protein to generate the protein HMM 150f. The protein HMM 150f is information defining each protein pair and the cooccurrence rate.

Figure 4:
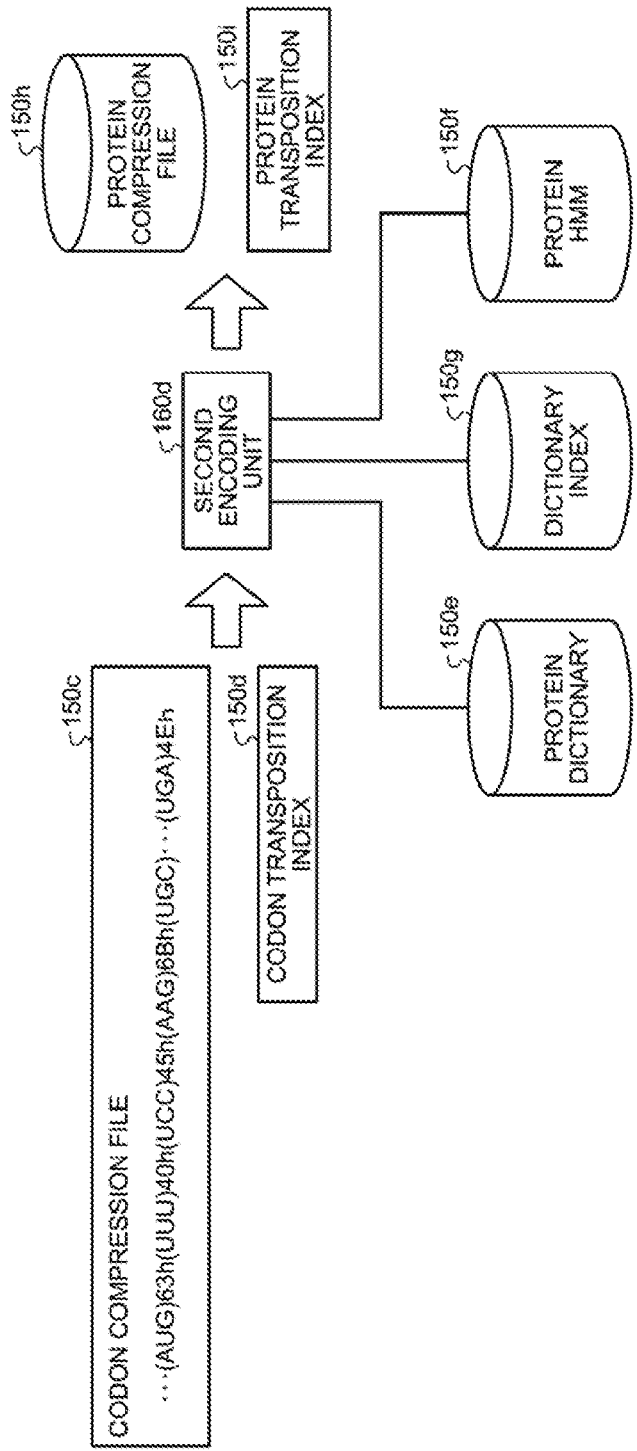
FIG. 4 is a diagram (4) for illustrating the processing by the identification apparatus according to the first example.

The following describes FIG. 4. A second encoding unit 160d of the identification apparatus generates a protein compression file 150h and a protein transposition index 150i based on the codon compression file 150c, the codon transposition index 150d, the protein dictionary 150e, the dictionary index 150g, and the protein HMM 150f. The second encoding unit 160d is an exemplary "identification unit."

The second encoding unit 160d identifies the break of the codon code sequence of each protein included in the codon compression file 150c based on the dictionary index 150g. Based on the codon code sequence between each break and protein dictionary 150e, the second encoding unit 160d identifies the protein code corresponding to the codon code sequence between each break and converts the codon code sequence into the protein code.

When the codon code sequence following the protein code (the break) corresponds to a plurality of protein codes, the second encoding unit 160d identifies a protein code having the highest cooccurrence rate among the corresponding protein codes based on the protein HMM 150f. The second encoding unit 160d converts the codon code sequence following the break into the identified protein code. The second encoding unit 160d repeatedly executes the above processing to generate the protein compression file 150h.

When generating the protein compression file 150h, the second encoding unit 160d generates the protein transposition index 150i. The protein transposition index 150i is information associating an offset from the top of the protein compression file 150h and the protein code with each other.

As described above, the identification apparatus according to the first example calculates the cooccurrence rate of a protein included in the codon compression file 150c and a protein following this protein to generate the protein HMM 150f. Using the protein HMM 150f, the identification apparatus can cut out the codon code sequence of the codon compression file 150c in units of correct proteins. Cutting out in units of correct proteins can generate the protein compression file 150h with the codon compression file 150c encoded in units of proteins. In addition, the sequence of the proteins included in the codon compression file 150c can be identified, and the primary structure of the proteins can easily be identified.

Figure 5:
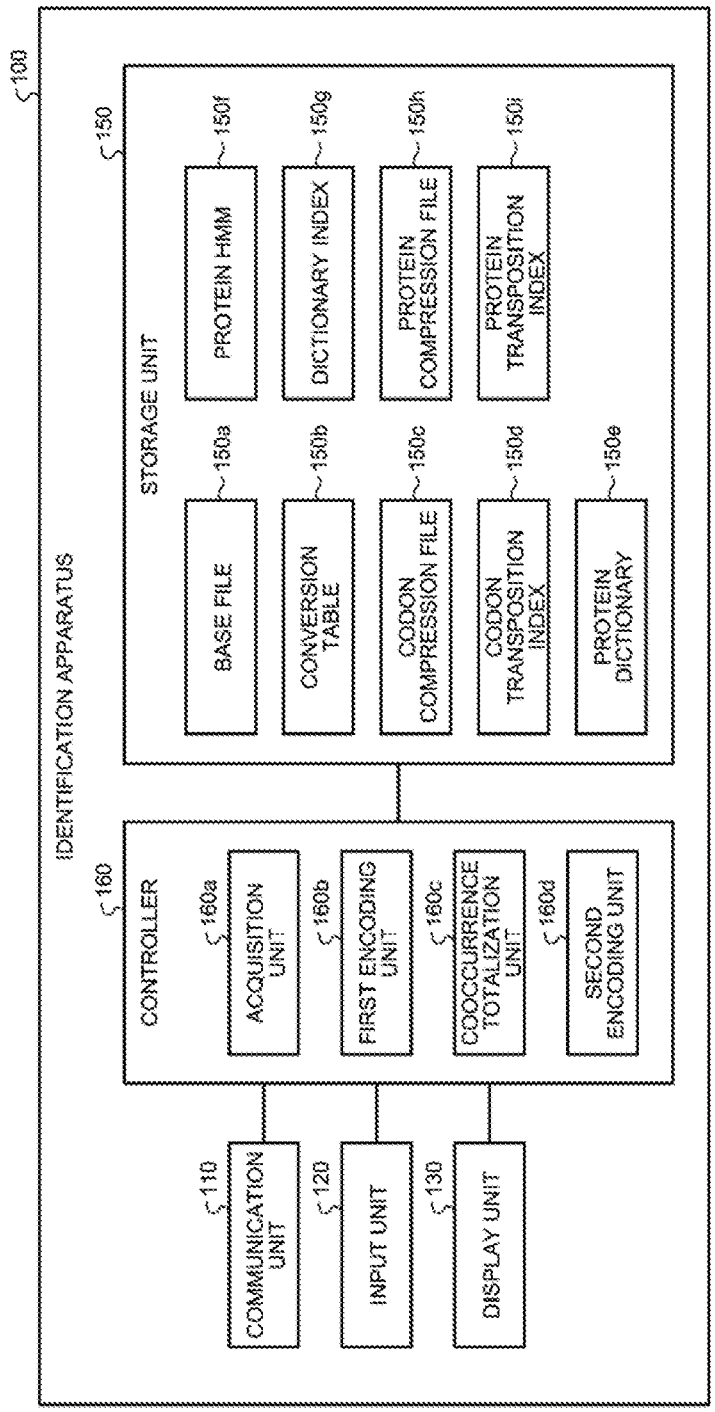
FIG. 5 is a functional block diagram of configuration of the identification apparatus according to the first example.

The following describes an exemplary configuration of an identification apparatus 100 according to the first example. FIG. 5 is a functional block diagram of a configuration of the identification apparatus according to the first example. As illustrated in FIG. 5, this identification apparatus 100 has a communication unit 110, an input unit 120, a display unit 130, a storage unit 150, and a controller 160.

The communication unit 110 is a processing unit executing data communication with another external apparatus (not illustrated) via a network. The communication unit 110 corresponds to a communication apparatus, for example. The communication unit 110 may receive the base file 150a described below and the like from the external apparatus, for example.

The input unit 120 is an input apparatus for receiving input of various kinds of information to the identification apparatus 100. The input unit 120 corresponds to a keyboard, a mouse, a touch panel, or the like, for example.

The display unit 130 is a display apparatus for displaying various kinds of information output from the controller 160. The display unit 130 corresponds to a liquid crystal display, a touch panel, or the like, for example.

The storage unit 150 has the base file 150a, the conversion table 150b, the codon compression file 150c, and the codon transposition index 150d. The storage unit 150 has the protein dictionary 150e, the protein HMM 150f, the dictionary index 150g, the protein compression file 150h, and the protein transposition index 150i. The storage unit 150 corresponds to a semiconductor memory element such as a random access memory (RAM), a read only memory (ROM), or a flash memory or a storage such as a hard disk drive (HDD).

The base file 150a is a file holding information in which a plurality of bases are arranged. The other description of the base file 150a is similar to the description of the base file 150a described in FIG. 1.

The conversion table 150b is a table associating a codon and a code corresponding to the codon with each other. FIG. 6 is a diagram of an exemplary data structure of the conversion table. As illustrated in FIG. 6, each codon and each code are associated with each other. The code of the codon "UUU" is "40h(01000000)," for example. The letter "h" indicates that it is a hexadecimal number.

The codon compression file 150c is a file holding information in which a plurality of encoded codons are arranged. The codon compression file 150c is generated by the first encoding unit 160b described below. The other description of the codon compression file is similar to the description of the codon compression file 150c described in FIG. 1.

Figure 7:
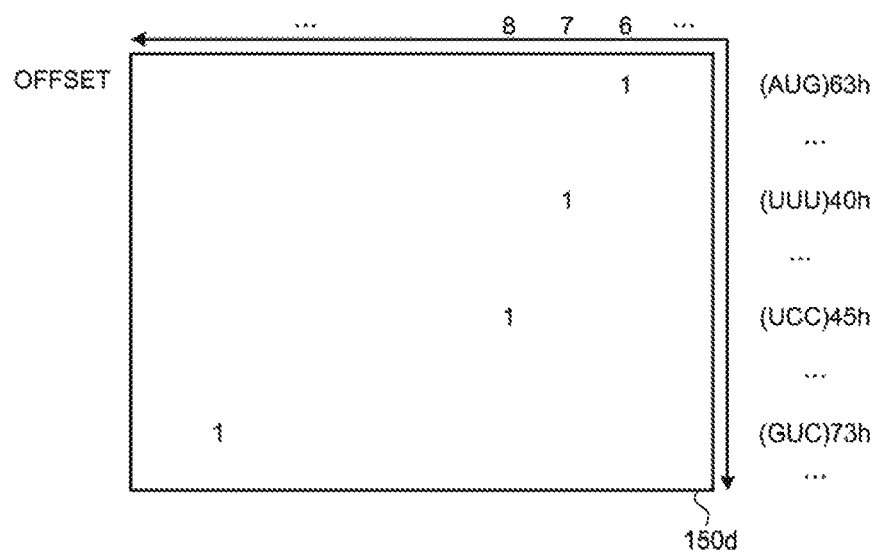
FIG. 7 is a diagram of an exemplary data structure of a codon transposition index.

The codon transposition index 150d is information associating the offset from the top of the codon compression file 150c and the codon type (the codon code) with each other. FIG. 7 is a diagram of an exemplary data structure of the codon transposition index. In FIG. 7, the horizontal axis of the codon transposition index 150d is an axis corresponding to the offset. The vertical axis of the codon transposition index 150d is an axis corresponding to the codon type (the codon code). The codon transposition index 150d is represented by a bitmap of "0" or "1," in which all bitmaps are set to "0" in an initial state.

It is assumed that the offset of the codon code at the top of the codon compression file 150c is "0," for example. When a codon code "(AUG)63h" is included at the seventh position from the top of the codon compression file 150c, the bit of a position at which the column of an offset "6" and the row of the codon code "(AUG)63h" cross each other of the codon transposition index 150d is "1."

The protein dictionary 150e is information associating protein information and the codon code sequence corresponding to the protein with each other. FIG. 8 is a diagram of an exemplary data structure of the protein dictionary. As illustrated in FIG. 8, this protein dictionary 150e associates the protein information, an amino acid code sequence, and the codon code sequence with each other.

The protein information includes a "code" of the protein, a "group" to which the protein belongs, and a "name" of the protein. The amino acid code sequence is a sequence of amino acid codes corresponding to the protein code (the protein type). The codon code sequence is a sequence of codon codes corresponding to the protein code (the protein type).

A protein "type I collagen" belongs to a group "collagen" and has a code of "8000h," for example. An amino acid code sequence corresponding to the code "8000h" is "02h46h59h•••03h." The codon code sequence is "02h63h78h•••03h."

The protein HMM 150f holds information on a cooccurrence rate of a protein and a protein following this protein. FIG. 9 is a diagram of an exemplary data structure of the protein HMM. As illustrated in FIG. 9, this protein HMM 150f associates protein information and cooccurring protein information with each other.

The protein information includes a "code" of the protein, a "group" to which the protein belongs, and a "name" of the protein. The protein code and the cooccurrence rate are associated with the cooccurring protein information. The following describes a record on the first row of the protein HMM 150f, for example. The probability (the cooccurrence rate) of a protein code following the protein code "8000h" being a code "8028h" is "78%." The probability (the cooccurrence rate) of the protein code following the protein code "8000h" being a code "8132h" is "63%." The probability (the cooccurrence rate) of the protein code following the protein code "8000h" being a code "80F5h" is "51%."

The dictionary index 150g is information holding the offset of the break of each codon code sequence (a mass of a codon code sequence corresponding to the protein) included in the codon compression file 150c. In the dictionary index 150g, each break is indicated by the offset from the top of the codon compression file 150c, for example. In the first example, the break is indicated by the offset of a top codon code of a following codon code sequence as an example. The break may be associated with the amino acid code sequence (hereinafter omitted) in addition to the codon code sequence.

The protein compression file 150h is a file holding information in which a plurality of protein codes are arranged. The protein compression file 150h is generated by the second encoding unit 160d described below. The other description of the protein compression file 150h is similar to the description of the protein compression file 150h described in FIG. 1.

Figure 10:
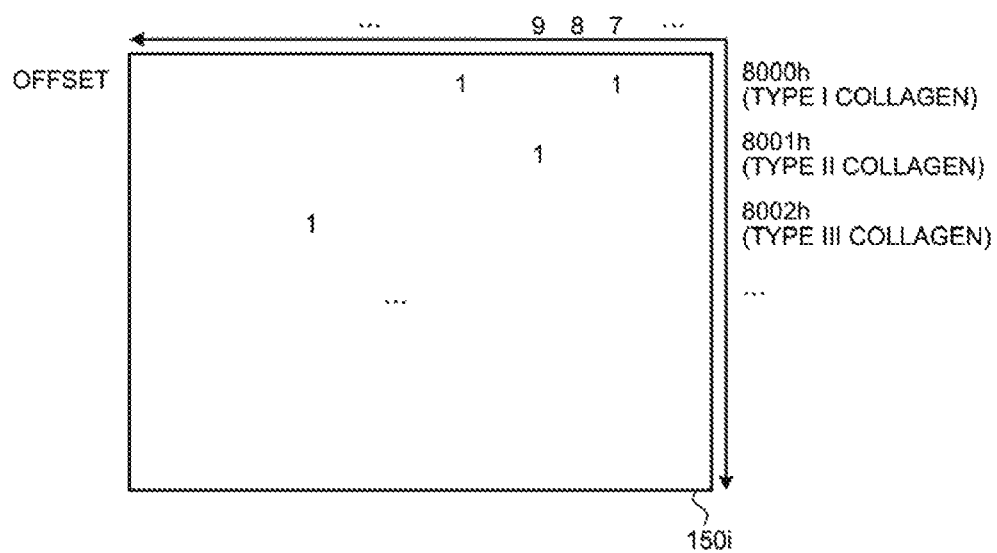
FIG. 10 is a diagram of an exemplary data structure of a protein transposition index.

The protein transposition index 150i is information associating the offset from the top of the protein compression file 150h and the protein type (the protein code) with each other. FIG. 10 is a diagram of an exemplary data structure of the protein transposition index. In FIG. 10, the horizontal axis of the protein transposition index 150i is an axis corresponding to the offset. The vertical axis of the protein transposition index 150i is an axis corresponding to the protein type (the protein code). The protein transposition index 150i is represented by a bitmap of "0" or "1," in which all bitmaps are set to "0" in an initial state.

It is assumed that the offset of the protein code at the top of the protein compression file 150h is "0," for example. When a protein code "8000h (type I collagen)" is included at the eighth position from the top of the protein compression file 150h, the bit of a position at which the column of an offset "7" and the row of the protein code "8000h. (type I collagen)" cross each other of the protein transposition index 150i is "1."

The following describes FIG. 5 again. The controller 160 has an acquisition unit 160a, the first encoding unit 160b, the cooccurrence totalization unit 160c, and the second encoding unit 160d. The controller 160 can be implemented by a central processing unit (CPU), a micro processing unit (MPU), or the like. The controller 160 can also be implemented by a hard-wired logic such as an application specific integrated circuit (ASIC) or a field programmable gate array (FPGA).

The acquisition unit 160a is a processing unit that acquires various kinds of information from a network-connected external apparatus (not illustrated) via the communication unit 110. When having acquired the base file 150a from the external apparatus, for example, the acquisition unit 160a stores the base file 150a in the storage unit 150. When the base file 150a is compressed with ZIP or the like, the acquisition unit 160a expands the compressed base file 150a.

The first encoding unit 160b is a processing unit generating the codon compression file 150c based on the base file 150a and the conversion table 150b. The first encoding unit 160b extracts bases in groups of three from the base file 150a and compares the extracted three bases and the conversion table 150b with each other to identify a code corresponding to three bases (a codon) and converts the three bases into the code. The first encoding unit 160b converts the codon "AUG" into a code "63h," for example. The first encoding unit 160b repeatedly executes the above processing to generate the codon compression file 150c.

When generating the codon compression file 150c, the first encoding unit 160b generates the codon transposition index 150d. The first encoding unit 160h sets "1" in a bitmap of the codon transposition index 150d corresponding to the converted codon code and the offset of the code of the codon compression file 150c, for example.

Figure 11:
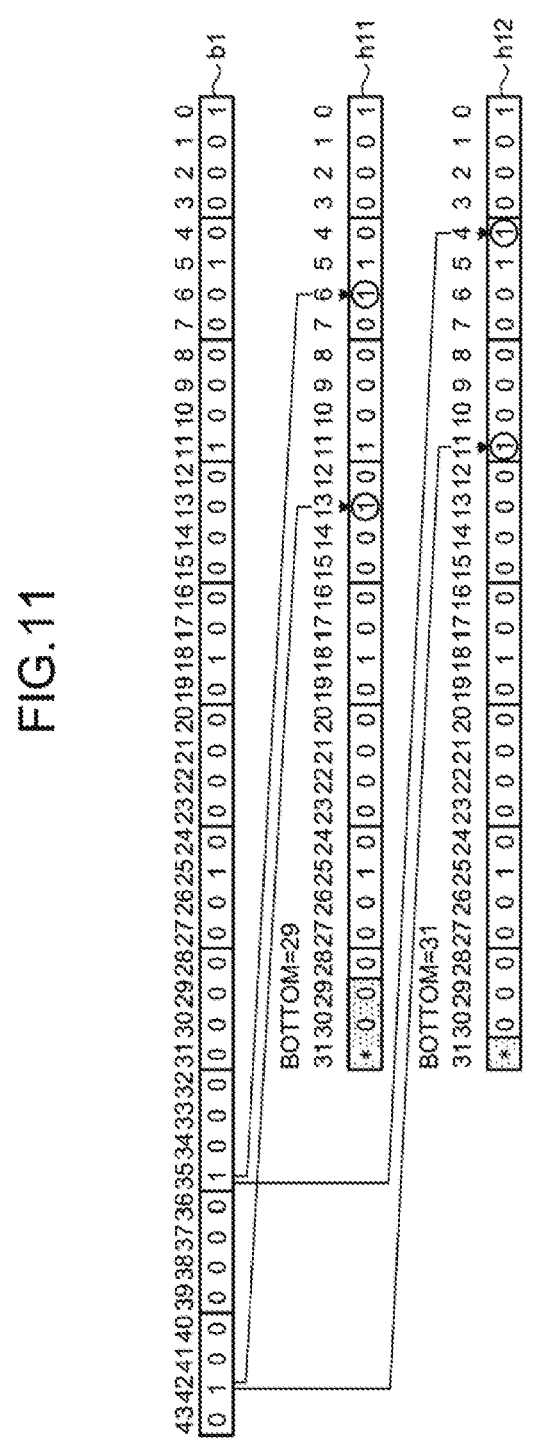

Upon generation of the codon transposition index 150d, the first encoding unit 160b may hash the codon transposition index 150d in order to reduce the amount of information. FIG. 11 is a diagram for illustrating exemplary processing to hash the codon transposition index.

The example illustrated in FIG. 11, assuming a 32-bit register, hashes bitmaps of respective rows of the codon transposition index 150d based on the prime number (bottom) of "29" and "31." The following describes a case of generating a hashed bitmap h11 and a hashed bitmap h12 from a bitmap b1 as an example.

The bitmap b1 indicates a bitmap as a result of extracting a certain row of a codon transposition index (e.g., the codon transposition index 150d illustrated in FIG. 7). The hashed bitmap h11 is a bitmap hashed by the bottom "29." The hashed bitmap h12 is a bitmap hashed by the bottom "31."

The first encoding unit 160b associates the remainder of a division of each bit position of the bitmap b1 by one bottom with the position of a hashed bitmap. When "1" is set at the corresponding bit position of the bitmap b1, the first encoding unit 160b performs processing to set "1" at the associated position of the hashed bitmap.

The following describes exemplary processing to generate the hashed bitmap h11 of the bottom "29" from the bitmap b1. First, the first encoding unit 160b copies information on positions "0 to 28" of die bitmap b1 to the hashed bitmap h11. Subsequently, the remainder of division of a bit position "35" of the bitmap b1 by the bottom "29" is "6," and the position "35" of the bitmap b1 is associated with a position "6" of the hashed bitmap h11. "1" is set at the position "35" of the bitmap h1, and the first encoding unit 160b sets "1" at the position "6" of the hashed bitmap h11.

The remainder of division of a bit position "42" of the bitmap h1 by the bottom "29" is "13," and the position "42" of the bitmap h1 is associated with a position "13" of the hashed bitmap h11. "1" is set at the position "42" of the bitmap b1, and the first encoding unit. 160b sets "1" at the position "13" of the hashed bitmap h11.

The first encoding unit 160b repeatedly executes the above processing for the positions of the position "29" and higher of the bitmap b1 to generate the hashed bitmap h11.

The following describes exemplary processing to generate the hashed bitmap h12 of the bottom "31" from the bitmap b1. First, the first encoding unit 160b copies information on positions "0 to 30" of the bitmap b1 to the hashed bitmap h12. Subsequently, the remainder of division of the bit position "35" of the bitmap h1 by the bottom "31" is "4,"

and the position "35" of the bitmap b1 is associated with a position "4" of the hashed bitmap h12. "1" is set at the position "35" of the bitmap b1, and the first encoding unit 160b sets "1" at the position "4" of the hashed bitmap h12.

The remainder of division of the bit position "42" of the bitmap h1 by the bottom "31" is "11," and the position "42" of the bitmap h1 is associated with a position "11" of the hashed bitmap h12. "1" is set at the position "42" of the bitmap h1, and the first encoding unit 160b sets "1" at the position "11" of the hashed bitmap h12.

The first encoding unit 160b repeatedly executes the above processing for the positions of the position "31" and higher of the bitmap b1 to generate the hashed bitmap h12.

The first encoding unit 160b performs compression by the above folding technique for each row of the codon transposition index 150d to hash the codon transposition index 150d. The hashed bitmaps of the bottoms "29" and "31" are given information on the row of a bitmap as a generation source (the encoded codon type).

The cooccurrence totalization unit 160c is a processing unit generating the protein HMM 150f and the dictionary index 150g based on the codon compression file 150c, the codon transposition index 150d, and the protein dictionary 150e.

The cooccurrence totalization unit 160c identifies the type and position of a protein included in the codon compression file 150c based on the codon transposition index 150d. The protein is a combination of certain codons (the codon code sequence), and the codon code sequence corresponding to the protein is defined in the protein dictionary 150e.

Figure 12:
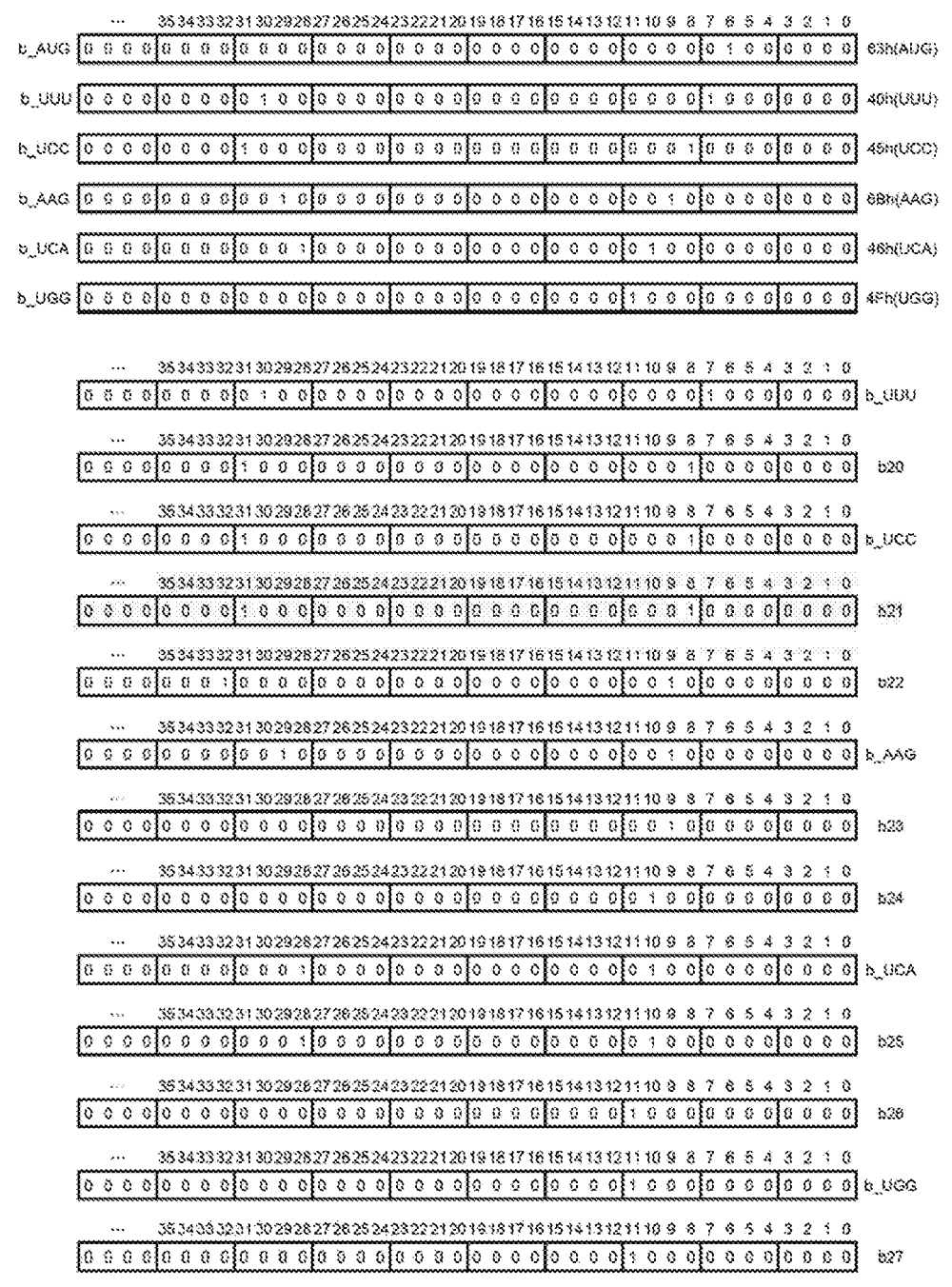

FIG. 12 is a diagram for illustrating exemplary processing to identify a protein included in the codon compression file by the cooccurrence totalization unit. The following describes a case in which the position of a protein "ααα" corresponding to a codon code sequence "(UUU)40h, (UCC) 45h, (AAG)613h, (UCA)46h, (UGG)4Fh" is identified as an example.

The cooccurrence totalization unit 160c refers to the codon transposition index 150d to acquire bitmaps corresponding to the respective codons "(UUU)40h, (UCC)45h, (PAG) 6Bh, (UCA) 46h, (UG)4Fh." The bitmap of the codon code "(UUU)40h" is defined as a bitmap b_UUU. The bitmap of the codon code "(UCC)45h" is defined as a bitmap b_UCC. The bitmap of the codon code "(AAG)6Bh" is defined as a bitmap b_AAG. The bitmap of the codon code "(UCA)46h" is defined as a bitmap b_UCA. The bitmap of the codon code "(UGG)4Fh" is defined as a bitmap b_UGG.

The cooccurrence totalization unit 160c acquires the bitmap b_UUU and left-shifts the bitmap b_UUU to generate a bitmap b20. The cooccurrence totalization unit 160c acquires the bitmap b_UCC and performs an AND operation of the bitmap b_UCC and the bitmap b20 to generate a bitmap b21. "1" is set at an offset "8" of the bitmap b21, which indicates that offsets 7 to 8 include the codons "(UUU)40h, (UCC)45h."

The cooccurrence totalization unit 160c left-shifts the bitmap b21 to generate a bitmap b22. The cooccurrence totalization unit 160c acquires the bitmap b_AAG and performs an AND operation of the bitmap b_ANG and the bitmap b22 to generate a bitmap b23. "1" is set at an offset "9" of the bitmap b23, which indicates that offsets 7 to 9 include the codons "(UUU)40h, (UCC)45h, (AAG)6Bh."

The cooccurrence totalization unit 160c left-shifts the bitmap b23 to generate a bitmap b24. The cooccurrence totalization unit 160c acquires the bitmap b_UCA and performs an AND operation of the bitmap b_UCA and the bitmap b24 to generate a bitmap b25. "1" is set at an offset "10" of the bitmap b25, which indicates that offsets 7 to 10 include the codons "(UUU)40h, (UCC) 45h, (AAG)6Bh, (UCA)46h."

The cooccurrence totalization unit 160c left-shifts the bitmap b25 to generate a bitmap b26. The cooccurrence totalization unit 160c acquires the bitmap b_UGG and performs an AND operation of the bitmap b_UGG and the bitmap b26 to generate a bitmap b27. "1" is set at an offset "11" of the bitmap b25, which indicates that offsets 7 to 11 include the codons "(UUU)40h, (UCC) 45h, (AAG) 6Bh, (UCA) 46h, (UGG)4Fh."

By executing the processing illustrated in FIG. 12, the cooccurrence totalization unit 160c determines that the offsets "7 to 11" of the codon compression file 150c include the codon code sequence "(UUU)40h, (UCC) 45h, (AAG) 6Bh, (UCA)46h, (UGG)4Fh" corresponding to the protein ααα. The cooccurrence totalization unit 160c repeatedly executes the above processing for the other proteins to identify the types and the positions (offsets) of the respective proteins included in the codon compression file 150c.

Subsequently, the cooccurrence totalization unit 160c generates the dictionary index 150g based on the offset of each protein included in the codon compression file 150c identified by the above processing. The cooccurrence totalization unit 160c sets the "break" of the codon code sequence corresponding to each protein included in the codon compression file 150c in the dictionary index 150g. The cooccurrence totalization unit 160c sets a flag "1" at an offset corresponding to the break in the dictionary index 150g, for example. In the initial value of the dictionary index 160g, the flag corresponding to each offset is "0."

In the process in which the cooccurrence totalization unit 160c executes the above processing, a codon code sequence from a certain offset of the codon compression file 150c may match a plurality of codon code sequences having different lengths included in the protein dictionary 150e.

As described in FIG. 3, for example, the codon code sequence from the offset P of the certain break of the codon compression file 150c to the offset $N_A$ may correspond to the code of the protein A, whereas the codon code sequence from the offset P to the offset $N_B$ may match the code of the protein B.

In this case, the cooccurrence totalization unit 160c sets the codon code of the offsets P to $P+N_A$ as the code of the protein A and sets a flag "1" at the offset $P+N_A+1$ in the dictionary index 150g. The cooccurrence totalization unit 160c sets the codon code of the offsets P to $P+N_B$ as the code of the protein B and sets a flag "1" at the offset $P+N^-_B+1$ in the dictionary index 150g. The cooccurrence totalization unit 160c repeatedly executes the above processing to generate the dictionary index 150g.

The following describes exemplary processing to generate the protein SIMM 150f by the cooccurrence totalization unit 160c. The cooccurrence totalization unit 160c identifies each protein code included in the codon compression file 150c based on the protein dictionary 150e. The cooccurrence totalization unit 160c totalizer the type of a protein code following a certain protein code to calculate a cooccurrence rate with the certain protein code.

It is assumed that the code of the protein A has appeared $M_A$ times in the codon compression file 150c, for example. When the code of the protein B among various kinds of protein codes following the code of the protein A has appeared $L_B$ times, the cooccurrence rate of the code of the protein. A and the code of the protein B is "$L_B/M_A \times 100$."
The cooccurrence totalization unit 160c repeatedly executes the processing to calculate the cooccurrence rate for the other proteins to generate the protein HMM 150*f*.

Figure 13:
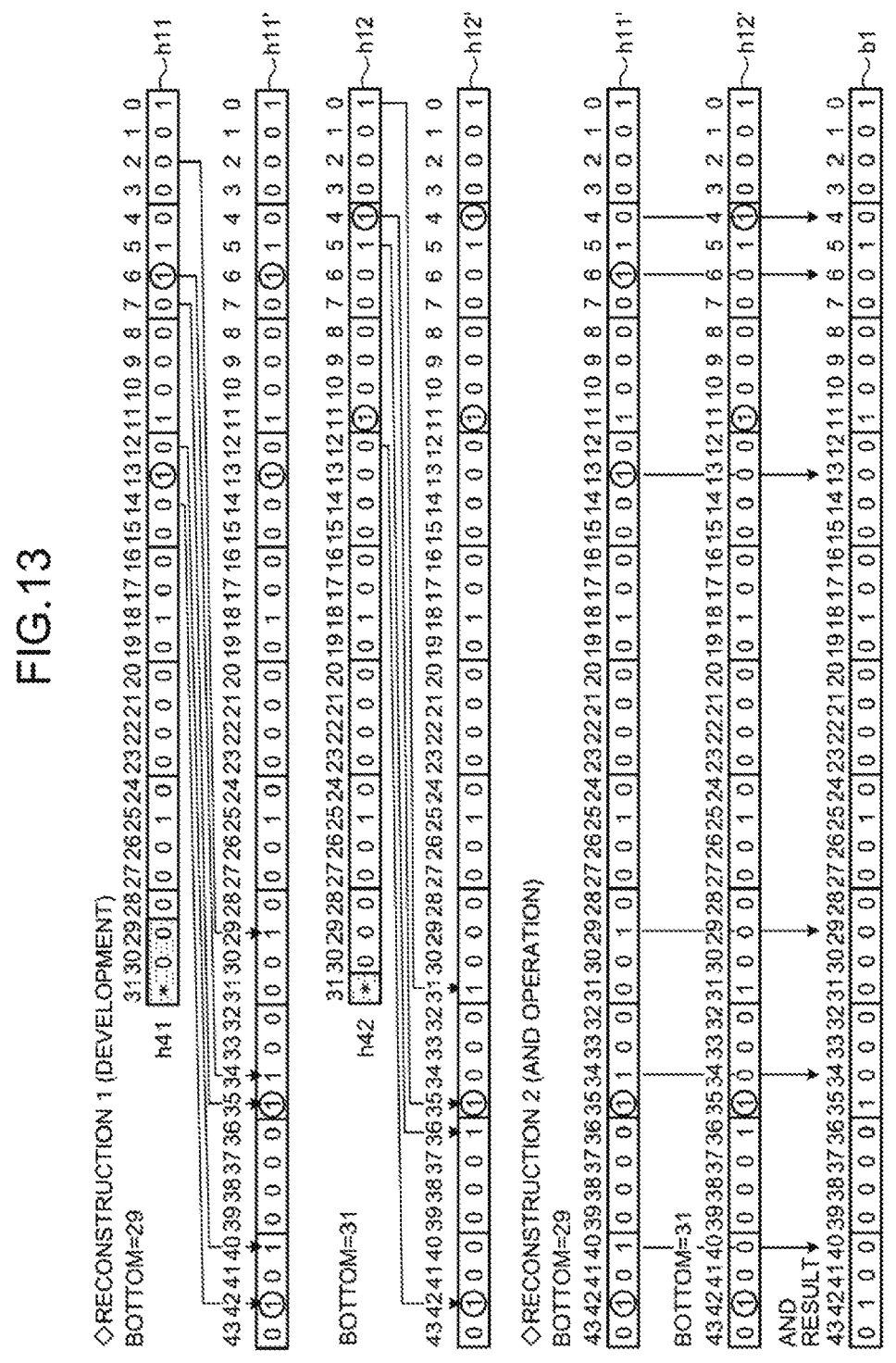

When the bitmap of the codon transposition index 150*d* is hashed, the cooccurrence totalization unit 160*c* reconstructs the hashed bitmap. FIG. 13 is a diagram for illustrating processing to reconstruct the hashed bitmap. The following describes a case in which the cooccurrence totalization unit 160*c* reconstructs the bitmap b1 based on the hashed bitmap h11 and the hashed bitmap h12 as an example.

The cooccurrence totalization unit 160*c* generates an intermediate bitmap h11' from the hashed bitmap h11 of the bottom "29." The cooccurrence totalization unit 160*c* copies the values of positions 0 to 28 of the hashed bitmap h11 to positions 0 to 28 of the intermediate bitmap h11', respectively.

The cooccurrence totalization unit 160*c* repeatedly executes processing to copy the values of the positions 0 to 28 of the hashed bitmap h11 to the values of a position 29 and subsequent positions of the intermediate bitmap h11', respectively, every "29." The example illustrated in FIG. 13 illustrates an example in which the values of the positions 0 to 14 of the hashed bitmap h11 are copied to positions 29 to 43 of the intermediate bitmap h11'.

The cooccurrence totalization unit 160*c* generates an intermediate bitmap h12' from the hashed bitmap h12 of the bottom "31." The cooccurrence totalization unit 160*c* copies the values of positions 0 to 30 of the hashed bitmap h12 to positions 0 to 30 of the intermediate bitmap h12', respectively.

The cooccurrence totalization unit 160*c* repeatedly executes processing to copy the values of the positions 0 to 30 of the hashed bitmap h12 to the values of a position 31 and subsequent positions of the intermediate bitmap h12', respectively, every "31." The example illustrated in FIG. 13 illustrates an example in which the values of the positions 0 to 12 of the hashed bitmap h12 are copied to positions 31 to 43 of the intermediate bitmap h12'.

Upon generation of the intermediate bitmap h11' and the intermediate bitmap h12', the cooccurrence totalization unit 160*c* performs an AND operation of the intermediate bitmap h11' and the intermediate bitmap h12' to reconstruct the bitmap b1 before hashing. The cooccurrence totalization unit 160*c* repeatedly executes similar processing for other hashed bitmaps and can thereby reconstruct each bitmap corresponding to the codon (reconstruct the codon transposition index 150*d*).

The following describes FIG. 5 again. The second encoding unit 160*d* generates the protein compression file 150*h* and the protein transposition index 150*i* based on the codon compression file 150*c*, the codon transposition index 150*d*, the protein dictionary 150*e*, the dictionary index 150*g*, and the protein HMM 150*f*.

The second encoding unit 160*d* identifies the break of the codon code sequence of each protein included in the codon compression file 150*c* based on the dictionary index 150*g*. Based on the codon code sequence between each break and the protein dictionary 150*e*, the second encoding unit 160*d* identifies the protein code corresponding to the codon code sequence between each break and converts the codon code sequence into the protein code.

When the codon code sequence following the protein code (the break) corresponds to a plurality of protein codes, the second encoding unit 160*d* identifies a protein code having the highest cooccurrence rate among the corresponding protein codes based on the protein HMM 150*f*.

The following describes processing by the second encoding unit 160*d* when the protein code following the protein code "8000h" is "8028h" or "8132h," for example. Referring to the protein HMM 150*f* described in FIG. 9, the cooccurrence rate of the protein code "8000h" and the code "8028h" is "78%," whereas the cooccurrence rate of the protein code "8000h" and the code "8132h" is "63%." The cooccurrence rate of the code "8000h" and the code "8028h" is larger than the cooccurrence rate of the code "8000h" and the code "8132h," and the second encoding unit 160*d* identifies the protein code following the protein code "8000h" as "8132h."

The second encoding unit 160*d* converts the codon code sequence following the break into the identified protein code. The second encoding unit 160*d* repeatedly executes the above processing to generate the protein compression file 150*h*.

When generating the protein compression file 150*h*, the second encoding unit 160*d* generates the protein transposition index 150*i*. The protein transposition index 150*i* is information associating the offset from the top of the protein compression file 150*h* and the protein code with each other. When generating the protein transposition index 150*i*, the second encoding unit 160*d* may hash the bitmap of the protein transposition index 150*i*. Processing to hash the bitmap of the protein transposition index 150*i* is similar to the processing to hash the bitmap of the codon transposition index 150*d* by the cooccurrence totalization unit 160*c*.

Figure 14:
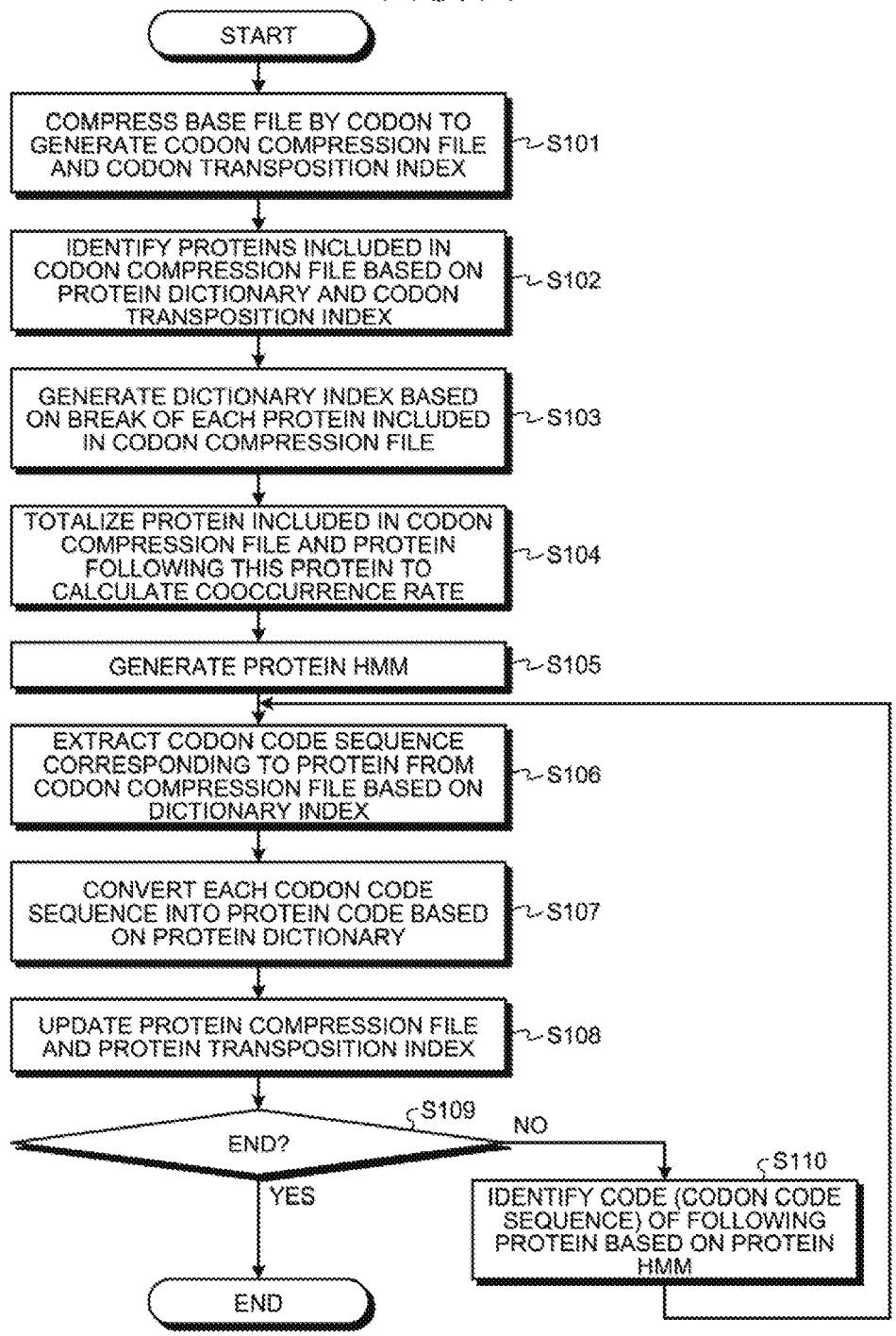
FIG. 14 is a flowchart of a processing procedure by the identification apparatus according to the first example.

The following describes an exemplary processing procedure by the identification apparatus 100 according to the first example. FIG. 14 is a flowchart of a processing procedure by the identification apparatus according to the first example. As illustrated in FIG. 14, the first encoding unit 160*b* of the identification apparatus 100 compresses the base file 150*a* by codon to generate the codon compression file 150*c* and a codon transposition index 150*d* (Step S101).

The cooccurrence totalization unit 160*c* identifies proteins included in the codon compression file 150*c* based on the protein dictionary 150*e* and the codon transposition index 150*d* (Step S102). The cooccurrence totalization unit 160*c* generates the dictionary index 150*g* based on the break of each protein included in the codon compression file 150*c* (Step S103).

The cooccurrence totalization unit 160*c* totalizes a protein included in the codon compression file 150*c* and a protein following this protein to calculate a cooccurrence rate (Step S104). The cooccurrence totalization unit 160*c* generates the protein HMM 150*f* (Step S105).

The second encoding unit 160*d* extracts the codon code sequence corresponding to the protein from the codon compression file 150*c* based on the dictionary index 150*g* (Step S106). The second encoding unit 160*d* converts the codon code sequence into the protein code based on the protein dictionary 150*e* (Step S107).

The second encoding unit 160*d* updates the protein compression file and the protein transposition index 150*i* (Step S108). If an end of the codon compression file 150*c* is reached (Yes at Step S109), the second encoding unit 160*d* ends the processing. If the end of the codon compression file 150*c* is not reached (No at Step S109), the second encoding unit 160*d* identifies the code (the codon code sequence) of the following protein based on the protein HMM 150*f* (Step S110) and shifts the process to Step S106.

The following describes the effects of the identification apparatus 100 according to the first example. The identification apparatus 100 calculates the cooccurrence rate of a protein included in the codon compression file 150*c* and a protein following this protein to generate the protein HMM 150*f*. Using the protein HMM 150*f*, the identification apparatus 100 can cut out the codon code sequence of the codon compression file 150c in units of correct proteins. Cutting out in units of correct proteins can generate the protein compression file 150h with the codon compression file 150c encoded in units of proteins. In addition, the sequence of the proteins included in the codon compression file 150c can be identified, and the primary structure of the proteins including a plurality of proteins or amino acids can easily be identified.

Using the protein HMM 150f, the identification apparatus 100 cuts out the codon code sequence of the codon compression file 150c in units of correct proteins and converts it into the code by protein to generate the protein compression file 150h. With this operation, the base file 150a can be compressed in units of proteins, and a compression rate can be increased compared with the codon compression file 150c.

The identification apparatus 100 generates the codon compression file 150c and the codon transposition index 150d based on the base file 150a and the conversion table 150b. Using the codon transposition index 150d, the arrangement of the codons included in the codon compression file 150c can be identified without being expanded.

When generating the protein compression file 150h, the identification apparatus 100 generates the protein transposition index 150i. Using this protein transposition index 150i, the arrangement of the proteins included in the protein compression file 150h can be identified without being expanded.

[b] Second Example

Figure 15:
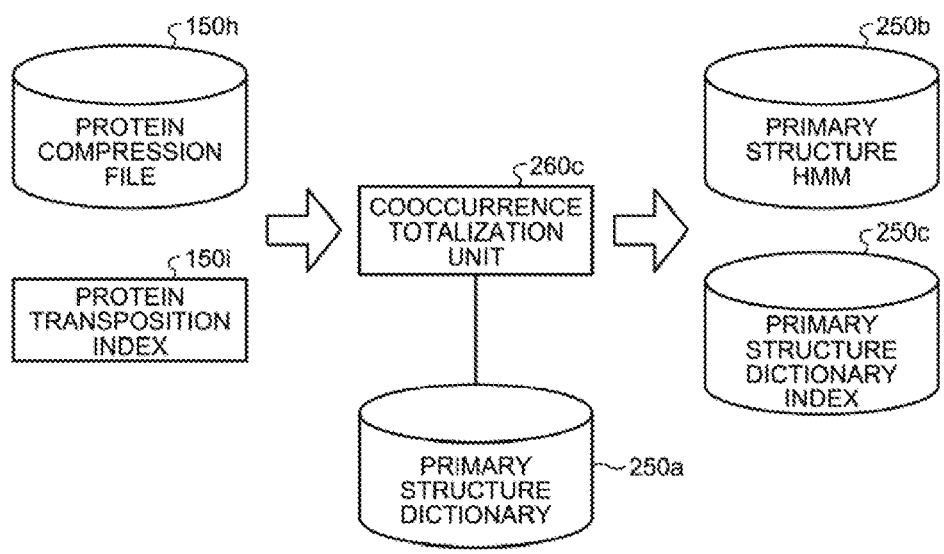
FIG. 15 is a diagram (1) for illustrating processing by an identification apparatus according to a second example.
Figure 16:
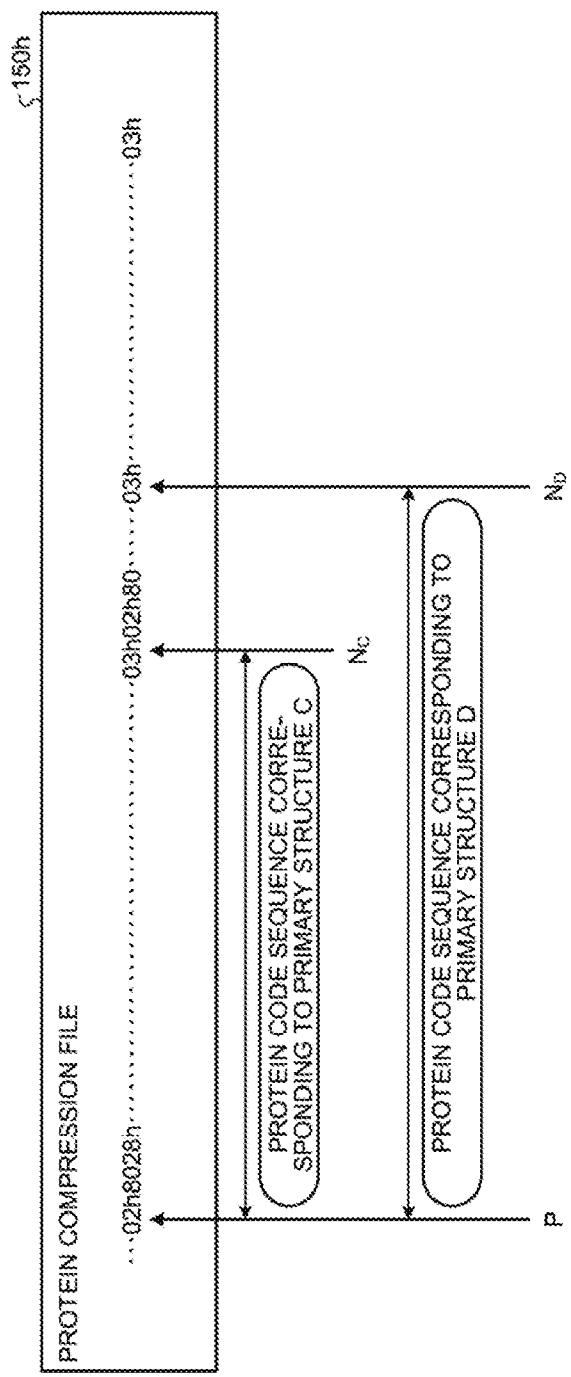
FIG. 16 is a diagram (2) for illustrating the processing by the identification apparatus according to the second example.
Figure 17:
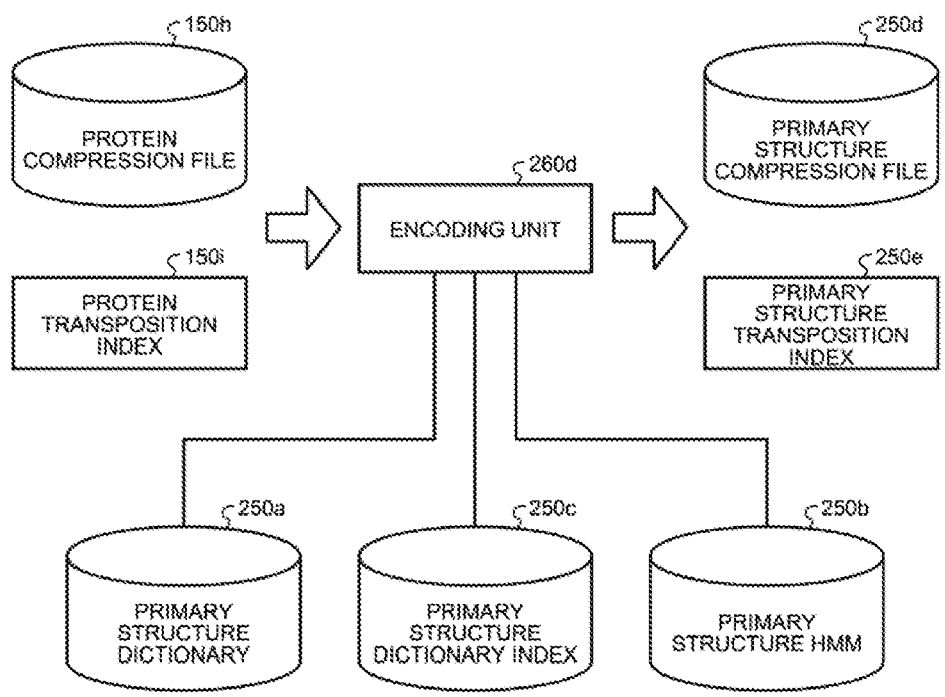
FIG. 17 is a diagram (3) for illustrating the processing by the identification apparatus according to the second example.

FIG. 15 to FIG. 17 are diagrams for illustrating processing by an identification apparatus according to a second example. The following first describes FIG. 15. A cooccurrence totalization unit 260c of the identification apparatus generates a primary structure HMM 250b and a primary structure dictionary index 250c based on the protein compression file 150h, the protein transposition index 150i, and a primary structure dictionary 250a.

Descriptions of the protein compression file 150h and the protein transposition index 150i are similar to the descriptions of the protein compression file 150h and the protein transposition index 150i described in the first example.

The primary structure dictionary 250a is information associating a protein primary structure code and a protein code sequence with each other. In the following description, the protein primary structure will be denoted simply as a "primary structure." The protein code sequence is information in which a plurality of protein codes are arranged. A combination of proteins (protein codes) varies in accordance with the protein primary structure, and the number of proteins corresponding to the primary structure varies.

The cooccurrence totalization unit 260c identifies a protein combination included in the protein compression file 150h based on the protein transposition index 150i. The cooccurrence totalization unit 260c repeatedly executes processing to compare the protein combination. (the protein code sequence) and the protein code sequence of the primary structure dictionary 250a with each other to identify primary structure codes included in the protein compression file 150h.

The cooccurrence totalization unit 260c, in the process of repeatedly executing the above processing, sets a "break" of the protein code sequence corresponding to each primary structure included in the protein compression file 150h in the primary structure dictionary index 250c.

In a protein code sequence "02h8028h••03h02h80F5h•03h," for example, the protein code sequence "02h8028h••03h" is a protein code sequence corresponding to a primary structure code "F00000h." The protein code sequence "02h80F5h•03h" is a protein code sequence corresponding to a primary structure code "F00001h." In this case, the gap between the protein code sequences "02h8028h••03h" and "02h80F5h•03h" is the "break." In the primary structure dictionary index 250c, each break is indicated by an offset from the top of the protein compression file 150h. In the second example, the break is indicated by the offset of a top code of a following protein code sequence as an example. In the above example, the offset of the top code <02h> of the following "02h80F5h•03h" is the offset of the break.

In the process in which the cooccurrence totalization unit 260c executes the above processing, a protein code sequence from a certain offset of the protein compression file 150h may match a plurality of protein code sequences having different lengths included in the primary structure dictionary 250a.

As illustrated in FIG. 16, for example, a protein code sequence from an offset P of a certain break of the protein compression file 150h to an offset $N_C$ may correspond to the code of a primary structure C, whereas a protein code sequence from the offset P to an offset $N_D$ may match the code of a primary structure D.

In this case, the cooccurrence totalization unit 260c sets the protein code sequence of offsets P to P+$N_C$ as the code of the primary structure C, sets an offset P+$N_C$+1 as a break, and repeatedly executes the above processing. The cooccurrence totalization unit 260c sets the protein code sequence of offsets P to P+$N_D$ as the code of the protein B, sets an offset P+$N_D$+1 as a break, and repeatedly executes the above processing.

The cooccurrence totalization unit 260c totalizer an amino acid combination included in an end of the primary structure for each primary structure (the protein code sequence of each primary structure) identified by the above processing to calculate a cooccurrence rate of a certain amino acid combination and the primary structure code. It is assumed that a certain amino acid combination E has appeared $M_E$ times in the protein compression file 150h, for example. When the appearance times of a primary structure F among the primary structures with the amino acid combination E as their ends is $L_P$ times, the cooccurrence rate of the amino acid combination E and the primary structure F is "$L_F/M_E \times 100$." The cooccurrence totalization unit 260c repeatedly executes the processing to calculate the cooccurrence rate for each amino acid combination to generate the primary structure HMM 250b. The primary structure HMM 250b is information defining the cooccurrence rate of the amino acid combination at the end of the primary structure and the primary structure.

The cooccurrence totalization unit 260c may identify the amino acid combination included in the end of the primary structure based on the relation between the protein code and the amino acid code sequence defined in the protein dictionary illustrated in FIG. 8.

The following describes FIG. 17. An encoding unit 260d of the identification apparatus generates a primary structure compression file 250d and a primary structure transposition index 250e based on the protein compression file 150h, the protein transposition index 150i, the primary structure dictionary 250a, the primary structure dictionary index 250c, and the primary structure HMM 250b. The encoding unit 260d is an exemplary "identification unit."

The encoding unit 260d identifies the break of the protein code sequence of each primary structure included in the protein compression file 150h based on the primary structure dictionary index 250c. Based on the protein code sequence between each break and the primary structure dictionary 250a, the encoding unit 260d identifies the primary structure code corresponding to the protein code sequence with the code of each break at the top and converts the protein code sequence into the primary structure code.

When the protein code sequence following the primary structure code (the break) corresponds to protein code sequences of a plurality of primary structures, the encoding unit 260d identifies a primary structure having the highest cooccurrence rate among the corresponding primary structures based on the primary structure HMM 250b. The encoding unit 260d converts the protein code sequence following the break into the identified primary structure code. The encoding unit 260d repeatedly executes the above processing to generate the primary structure compression file 250d.

The following describes the processing by the encoding unit 260d with reference to FIG. 16, for example. It is assumed that the protein code sequence with the offset P at the top corresponds to the protein code sequence corresponding to the primary structure C and the protein code sequence corresponding to the primary structure D as an example. In this case, the encoding unit 260d compares a cooccurrence rate CO1 of an amino acid combination with the offset $N_C$ of the primary structure C as an end and the primary structure C and a cooccurrence rate CO2 of an amino acid combination with the offset $N_D$ of the primary structure D as an end and the primary structure D with each other.

When the cooccurrence rate CO1 is larger than the cooccurrence rate CO2, the encoding unit 260d identifies that the protein code sequence with the offset P at the top is the protein code sequence corresponding to the primary structure C and converts the protein code sequence of offsets P to $N_C$ into the code of the primary structure C. The encoding unit 260d repeatedly executes the above processing for the protein code sequence with the offset $N_C$ at the top.

On the other hand, when the cooccurrence rate CO2 is larger than the cooccurrence rate CO1, the encoding unit. 260d identifies that the protein code sequence with the offset P at the top is the protein code sequence corresponding to the primary structure D and converts the protein code sequence of offsets P to $N_D$ into the code of the primary structure D. The encoding unit 260d repeatedly executes the above processing for the protein code sequence with the offset $N_D$ at the top.

When generating the primary structure compression file 250d, the encoding unit 260d generates the primary structure transposition index 250e. The primary structure transposition index 250e is information associating an offset from the top of the primary structure compression file 250d and the primary structure code with each other.

As described above, the identification apparatus according to the second example calculates the cooccurrence rate of a primary structure included in the protein compression file 150h and an amino acid combination included in the end of this primary structure to generate the primary structure HMM 250b. Using the primary structure HMM 250b, the identification apparatus can appropriately identify each primary structure included in the protein code sequence of the protein compression file 150h. Each primary structure included in the protein compression file 150h is identified, whereby the protein compression file 150h can be encoded in units of primary structures.

Figure 18:
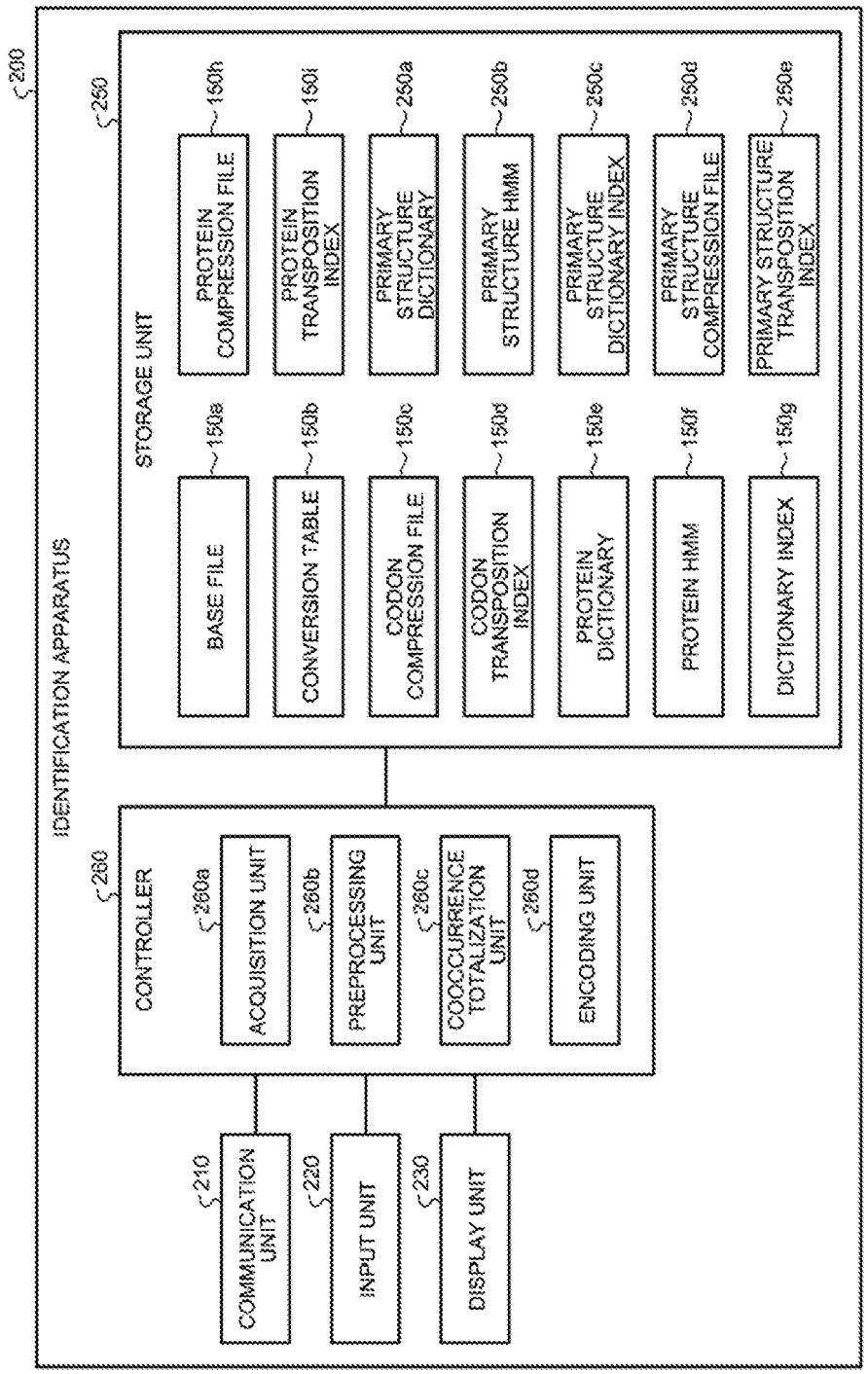
FIG. 18 is a functional block diagram of a configuration of the identification apparatus according to the second example.

The following describes an exemplary configuration of an identification apparatus 200 according to the second example. FIG. 18 is a functional block diagram of a configuration of the identification apparatus according to the second example. As illustrated in FIG. 18, this identification apparatus 200 has a communication unit 210, an input unit 220, a display unit 230, a storage unit 250, and a controller 260.

Descriptions of the communication unit 210, the input unit 220, and the display unit 230 are similar to the descriptions of the communication unit 110, the input unit 120, and the display unit 130 described in the first example.

The storage unit 250 has the base file 150a, the conversion table 150b, the codon compression file 150c, and the codon transposition index 150d. The storage unit 250 has the protein dictionary 150e, the protein HMM 150f, the dictionary index 150g, the protein compression file 150h, and the protein transposition index 150i. The storage unit 250 has the primary structure dictionary 250a, the primary structure HMM 250b, the primary structure dictionary index 250c, the primary structure compression file 250d, and the primary structure transposition index. 250e. The storage unit 250 corresponds to a semiconductor memory element such as a RAM, a ROM, or a flash memory or a storage such as an HDD.

Descriptions of the base file 150a, the conversion table 150b, the codon compression file 150c, and the codon transposition index 150d are similar to those described in the first example. Descriptions of the protein dictionary 150e, the protein HMM 150f, the dictionary index 150g, the protein compression file 150h, and the protein transposition index 150i are similar to those described in the first example.

The primary structure dictionary 250a is information associating the primary structure code and the protein code sequence with each other. FIG. 19 is a diagram of an exemplary data structure of the primary structure dictionary. As illustrated in FIG. 19, this primary structure dictionary 250a associates primary structure information and the protein code sequence with each other.

The primary structure information includes a "code" of the primary structure, a "group" to which the primary structure belongs, and a "name" of the primary structure. The protein code sequence is a sequence of a protein code corresponding to the primary structure code (a primary structure type).

A primary structure "α primary sequence" belongs to a group "G1" and has a code of "F00000h," for example. A protein code sequence corresponding to the code "F00000h" is "02h8028h•••03h."

The primary structure HMM 250b is information defining the cooccurrence rate of the amino acid combination at the end of the primary structure and the primary structure. FIG. 20 is a diagram of an exemplary data structure of the primary structure HMM. As illustrated in FIG. 20, this primary structure HMM 250b associates amino acid combination information and cooccurring primary structure information with each other.

Each "code" corresponding to the amino acid combination and a "name" of each amino acid included in the amino acid combination are associated with the amino acid combination information. The primary structure code and the cooccurrence rate are associated with the cooccurring primary structure information. The following describes a record on the first row of the primary structure HMM 250b, for example. The cooccurrence rate of an amino acid combination at the end "47h41h50h" and a primary structure code "F08028h" is "78%." The cooccurrence rate of an amino acid combination at the end "47h41h50h" and a primary structure code "F08132h" is "63%." The cooccurrence rate of an amino acid combination at the end "47h41h50h" and a primary structure code "F080F5h" is "51%."

The primary structure dictionary index 250c is information holding the offset of the break of each protein code sequence (a mass of the protein code sequence corresponding to the primary structure) included in the protein transposition index 150i. In the primary structure dictionary index 250c, each break is indicated by the offset from the top of the protein compression file 150h, for example. In the second example, the break is indicated by the offset of a top protein code of a following protein code sequence as an example.

The primary structure compression file 250d is a file holding information in which a plurality of primary structure codes are arranged. The primary structure compression file 250d is generated by the encoding unit 260d described below. The other description of the primary structure compression file 250d is similar to the description of the primary structure compression file 250d described in FIG. 17.

Figure 21:
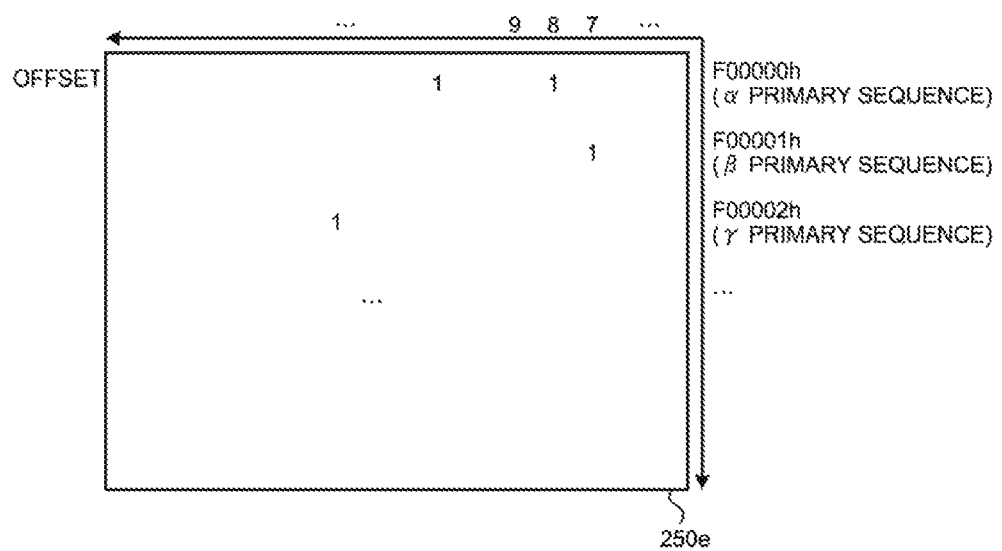
FIG. 21 is a diagram of an exemplary data structure of a primary structure transposition index.

The primary structure transposition index 250e is information associating the offset from the top of the primary structure compression file 250d and the primary structure type (the primary structure code) with each other. FIG. 21 is a diagram of an exemplary data structure of the primary structure transposition index. In FIG. 21, the horizontal axis of the primary structure transposition index 250e is an axis corresponding to the offset. The vertical axis of the primary structure transposition index is an axis corresponding to the primary structure type (the primary structure code). The primary structure transposition index 250e is represented by a bitmap of "0" or "1," in which all bitmaps are set to "0" in an initial state.

It is assumed that the offset of the primary structure code at the top of the primary structure compression file 250d is "0," for example. When a primary structure code "F00000h (α primary sequence)" is included at the ninth position from the top of the primary structure compression file 250d, the bit of a position at which the column of an offset "8" and the row of the primary structure code "F00000h (α primary sequence)" cross each other of the primary structure transposition index 250e is "1."

The following describes FIG. 18 again. The controller 260 has an acquisition unit 260a, a preprocessing unit 260b, the cooccurrence totalization unit 260c, and the encoding unit 260d. The controller 260 can be implemented by a CPU, an MPU, or the like. The controller 260 can also be implemented by a hard-wired logic such as an ASIC or an FPGA.

The acquisition unit 260a is a processing unit that acquires various kinds of information from a network-connected external apparatus (not illustrated) via the communication unit 210. When having acquired the base file 150a from the external apparatus, for example, the acquisition unit 260a stores the base file 150a in the storage unit 250. When the base file 150a is compressed with ZIP or the like, the acquisition unit 260a expands the compressed base file 150a.

The preprocessing unit 260b is a processing unit corresponding to the first encoding unit 160b, the cooccurrence totalization unit 160c, and the second encoding unit 160d described in the first example. The preprocessing unit 260b executes processing corresponding to the first encoding unit 160b, the cooccurrence totalization unit 160c, and the second encoding unit 160d to generate the protein compression file 150h and the protein transposition index 150i.

The cooccurrence totalization unit 260c is a processing unit generating the primary structure HMM 250b and the primary structure dictionary index 250c based on the protein compression file 150h, the protein transposition index 150i, and the primary structure dictionary 250a.

The cooccurrence totalization unit 260c identifies the type and position of a primary structure included in the protein compression file 150h based on the protein transposition index 150i. The primary structure is a combination of certain proteins (the protein code sequence), and the protein code sequence corresponding to the primary structure is defined in the primary structure dictionary 250a.

The cooccurrence totalization unit 260c extracts the bitmap of a protein included in a certain primary structure from the protein transposition index 150i and repeatedly executes left-shifting and AND operation to identify the position of the certain primary structure. Descriptions of the left-shifting and the AND operation executed by the cooccurrence totalization unit 260c are similar to those of the cooccurrence totalization unit 160c described in the first example. The cooccurrence totalization unit 260c repeatedly executes the above processing to identify each primary structure included in the protein compression file 150h.

In the process in which the cooccurrence totalization unit 260c executes the above processing, a protein code sequence from a certain offset of the protein compression file 150h may match a plurality of protein code sequences having different lengths included in the primary structure dictionary 250a.

As described in FIG. 16, for example, the protein code sequence from the offset P of the certain break of the protein compression file 150h to the offset $N_C$ may correspond to the code of the primary structure C, whereas the protein code sequence from the offset P to the offset $N_D$ may match the code of the primary structure D, for example.

In this case, the cooccurrence totalization unit 260c sets the protein code sequence of the offsets P to $P+N_C$ as the code of the primary structure C and sets a flag "1" at the offset $P+N_C+1$ of the primary structure dictionary index 250c. The cooccurrence totalization unit 260c sets the protein code sequence of the offsets P to $P+N_D$ as the code of the primary structure D and sets a flag "1" at the offset $P+N_D+1$ of the primary structure dictionary index 250c. The cooccurrence totalization unit 260c repeatedly executes the above processing to generate the primary structure dictionary index 250c.

The following describes exemplary processing to generate the primary structure HMM 250b by the cooccurrence totalization unit 260c. The cooccurrence totalization unit 260c identifies each primary structure code included in the protein compression file 150h based on the primary structure dictionary. The cooccurrence totalization unit 260c totalizes the amino acid combination included in the end of the primary structure for each primary structure.

It is assumed that the certain amino acid combination E has appeared $M_E$ times in the protein compression file 150h, for example. When the appearance times of the primary structure F among the primary structures with the amino acid combination E as their ends is $L_F$ times, the cooccurrence rate of the amino acid combination E and the primary structure F is "$L_F/M_E \times 100$." The cooccurrence totalization unit 260c repeatedly executes the processing to calculate the cooccurrence rate for each amino acid combination to generate the primary structure. HMM 250b. The cooccurrence totalization unit 260c identifies the amino acid code sequence (the amino acid combination) corresponding to the protein based on the protein dictionary 150e.

The end part in which the cooccurrence totalization unit 260c identifies the amino acid combination is a part with a certain number of amino acids from the end toward the top. The end part may be set in advance.

The encoding unit 260d generates the primary structure compression file 250d and the primary structure transposition index 250e based on the protein compression file 150h, the protein transposition index 150i, the primary structure dictionary 250a, the primary structure dictionary index 250c, and the primary structure HMM 250b.

The encoding unit 260d identifies the break of the protein code sequence of each primary structure included in the protein compression file 150h based on the primary structure dictionary index 250c. Based on the protein code sequence between each break and the primary structure dictionary 250a, the encoding unit 260d identifies the primary structure code corresponding to the protein code sequence between each break and converts the protein code sequence into the primary structure code.

When the protein code sequence following the primary structure code (the break) corresponds to a plurality of primary structure codes, the encoding unit 260d identifies a primary structure having the highest cooccurrence rate among the corresponding primary structure codes based on the primary structure HMM 250b. The encoding unit 260d converts the protein code sequence following the break into the identified primary structure code. The encoding unit 260d repeatedly executes the above processing to generate the primary structure compression file 250d.

The following describes the processing by the encoding unit 260d with reference to FIG. 16, for example. It is assumed that the protein code sequence with the offset P at the top corresponds to the protein code sequence corresponding to the primary structure C and the protein code sequence corresponding to the primary structure D. In this case, the encoding unit 260d compares the cooccurrence rate CO1 of the amino acid combination with the offset $N_C$ of the primary structure C as the end and the primary structure C and the cooccurrence rate CO2 of the amino acid combination with the offset $N_D$ of the primary structure D as the end and the primary structure with each other.

When the cooccurrence rate CO1 is larger than the cooccurrence rate CO2, the encoding unit 260d identifies that the protein code sequence with the offset P at the top is the protein code sequence corresponding to the primary structure C and converts the protein code sequence of the offsets P to $N_C$ into the code of the primary structure C. The encoding unit 260d repeatedly executes the above processing for the protein code sequence with the offset $N_C$ at the top.

On the other hand, when the cooccurrence rate CO2 is larger than the cooccurrence rate CO1, the encoding unit 260d identifies that the protein code sequence with the offset P at the top is the protein code sequence corresponding to the primary structure D and converts the protein code sequence of the offsets P to N into the code of the primary structure D. The encoding unit 260d repeatedly executes the above processing for the protein code sequence with the offset $N_D$ at the top.

When generating the primary structure compression file 250d, the encoding unit 260d generates the primary structure transposition index 250e. The primary structure transposition index 250e is information associating the offset from the top of the primary structure compression file 250d and the primary structure code with each other.

Figure 22:
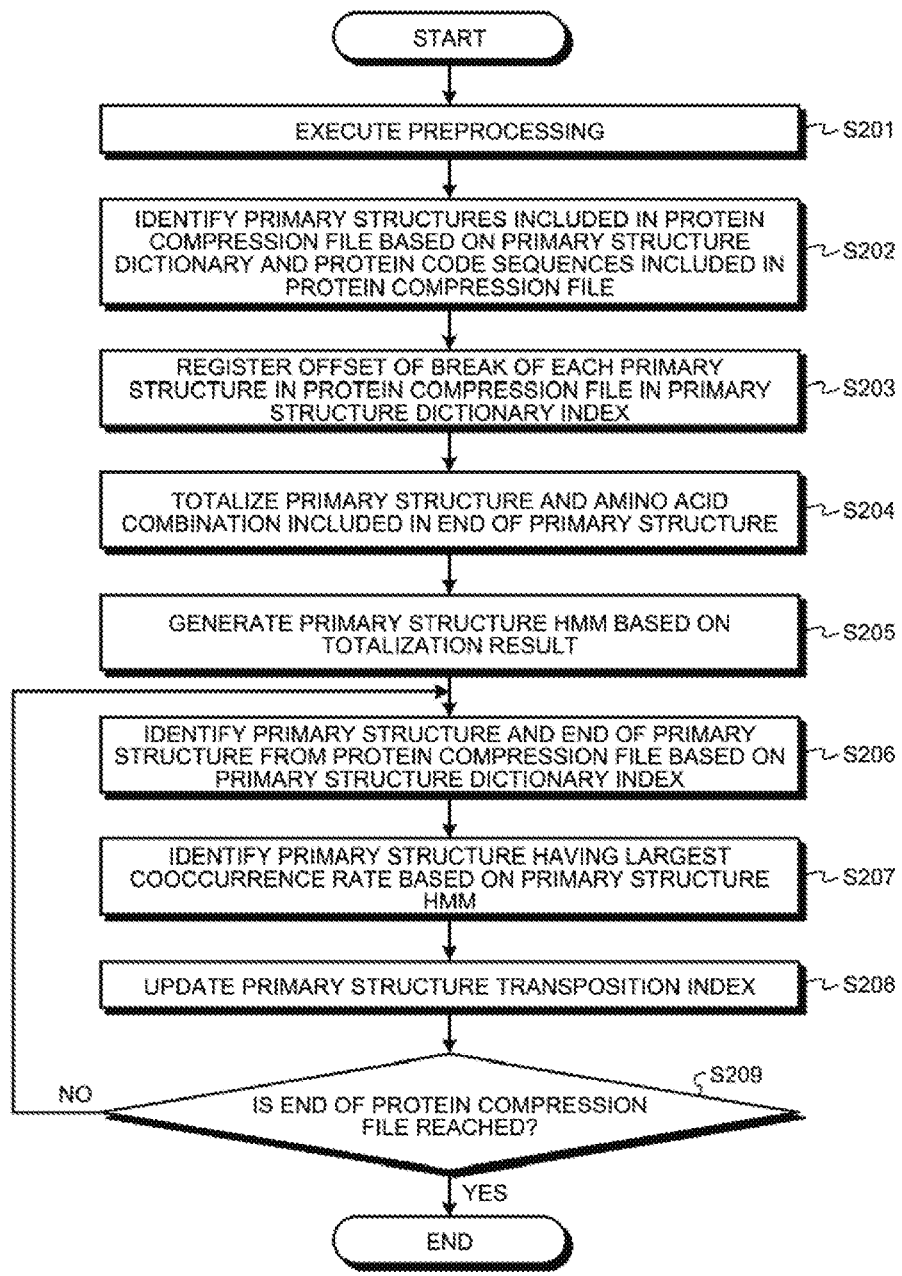
FIG. 22 is a flowchart of a processing procedure by the identification apparatus according to the second example.

The following describes an exemplary processing procedure by the identification apparatus 200 according to the second example. FIG. 22 is a flowchart of a processing procedure by the identification apparatus according to the second example. As illustrated in FIG. 22, the preprocessing unit 260b of the identification apparatus 200 executes preprocessing to generate the protein compression file 150h and the protein transposition index 150i (Step S201). The preprocessing at Step S201 corresponds to the processing described in FIG. 14 in the first example.

The cooccurrence totalization unit 260c of the identification apparatus 200 identifies primary structures included in the protein compression file 150h based on the primary structure dictionary 250a and the protein code sequences included in the protein compression file 150h (Step S202).

The cooccurrence totalization unit 260c registers the offset of the break of each primary structure in the protein compression file 150h in the primary structure dictionary 250a (Step S203). The cooccurrence totalization unit 260c totalizes the primary structure and the amino acid combination included in the end of the primary structure (Step S204). The cooccurrence totalization unit 260c generates the primary structure HMM 250b based on a totalization result (Step S205).

The encoding unit 260d of the identification apparatus 200 identifies the primary structure and the end of the primary structure (the amino acid combination) from the protein compression file 150h based on the primary structure dictionary index 250c (Step S206).

The encoding unit 260d identifies a primary structure having the largest cooccurrence rate based on the primary structure HMM 250b (Step S207). The encoding unit 260d updates the primary structure transposition index 250e (Step S208).

When an end of the protein compression file 150h is reached (Yes at Step S209), the encoding unit 260d ends the processing. On the other hand, when the end of the protein compression file 150h is not reached (No at Step S209), the encoding unit 260d shifts the process to Step S206.

The following describes the effects of the identification apparatus 200 according to the second example. The identification apparatus 200 calculates the cooccurrence rate of a primary structure included in the protein compression file 150h and an amino acid combination included in the end of this primary structure to generate the primary structure HMM 250b. Using the primary structure HMM 250b, the identification apparatus 200 can appropriately identify each primary structure included in the protein code sequence of the protein compression file 150h. Each primary structure included in the protein compression file 150h is identified, whereby the protein compression file 150h can be encoded in units of primary structures.

Figure 23:
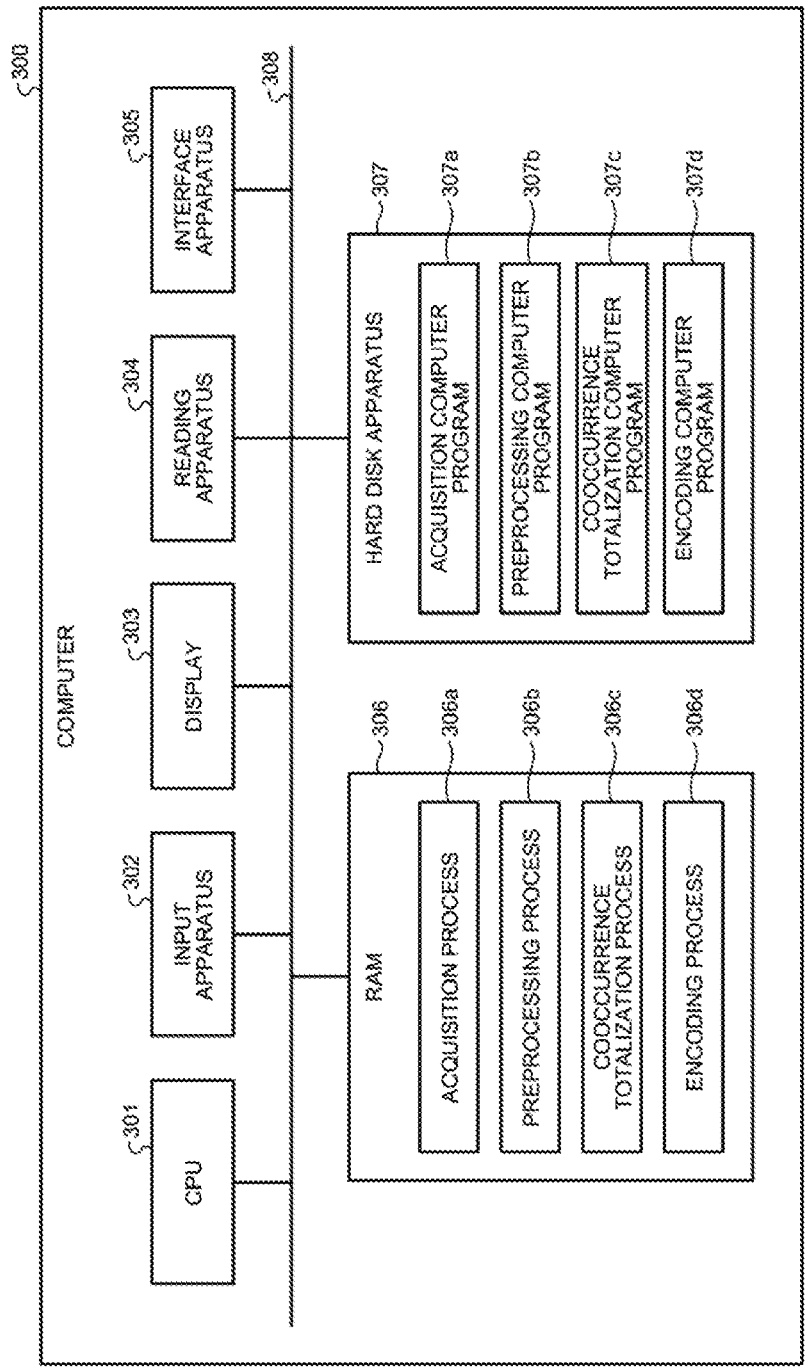
FIG. 23 is a diagram of an exemplary hardware configuration of a computer implementing functions similar to those of the identification apparatuses according to the examples.

The following describes an exemplary hardware configuration of a computer implementing functions similar to those of the identification apparatus 200 (100) demonstrated in the examples. FIG. 23 is a diagram of an exemplary hardware configuration of a computer implementing functions similar to those of the identification apparatuses according to the examples.

As illustrated in FIG. 23, this computer 300 has a CPU 301 executing various kinds of computation processing, an input apparatus 302 receiving input of data from a user, and a display 303. The computer 300 has a reading apparatus 304 reading computer programs and the like from a storage medium and an interface apparatus 305 delivering and receiving data to and from an external apparatus or the like via a wired or wireless network. The computer 300 has a RAM 306 temporarily storing therein various kinds of information and a hard disk apparatus 307. The apparatuses 301 to 307 are connected to a bus 308.

The hard disk apparatus 307 has an acquisition computer program 307a, a preprocessing computer program 307b, a cooccurrence totalization computer program 307c, and an encoding computer program 307d. The CPU 301 reads the acquisition computer program 307a, the preprocessing computer program 307b, the cooccurrence totalization computer program 307c, and the encoding computer program 307d to develop them in the RAM 306.

The acquisition computer program 307a functions as an acquisition process 306a. The preprocessing computer program 307b functions as a preprocessing process 306b. The cooccurrence totalization computer program 307c functions as a cooccurrence totalization process 306c. The encoding computer program 307d functions as an encoding process 306d.

Processing by the acquisition process 306a corresponds to processing by the acquisition unit 260a. Processing by the preprocessing process 306b corresponds to processing by the preprocessing unit 260b. Processing by the preprocessing unit 260b corresponds to processing by the first encoding unit 160b, the cooccurrence totalization unit 160c, and the second encoding unit 160d. Processing by the cooccurrence totalization process 306c corresponds to processing by the cooccurrence totalization unit 260c. Processing by the encoding process 306d corresponds to processing by the encoding unit 260d.

The computer programs 307a to 307d are not necessarily needed to be stored in the hard disk apparatus 307 from the beginning. The computer programs are stored in a "portable physical medium" such as a flexible disk (FD), a compact disc read only memory (CD-ROM), a digital versatile disc (DVD), a magneto-optical disc, or an IC card to be inserted into the computer 300, for example; the computer 300 may read and execute the computer programs 307a to 307d.

The primary structure of proteins included in a genome can be identified.

All examples and conditional language recited herein are intended for pedagogical purposes of aiding the reader in understanding the invention and the concepts contributed by the inventor to further the art, and are not to be construed as limitations to such specifically recited examples and conditions, nor does the organization of such examples in the specification relate to a showing of the superiority and inferiority of the invention. Although the embodiments of the present invention have been described in detail, it should be understood that the various changes, substitutions, and alterations could be made hereto without departing from the spirit and scope of the invention.

What is claimed is:

1. A method of identification comprising:
    acquiring a protein file in which a plurality of proteins including a plurality of amino acids are arranged, using a processor;
    first identifying a plurality of primary structure candidates with any position included in the protein file as a starting position, and identifying an end of each of the primary structure candidates based on a primary structure dictionary index that indicates a position of a primary structure included in the protein file, using the processor;
    second identifying one primary structure among the primary structure candidates based on a combination of a primary structure and each amino acid and a primary structure table, where each amino acid is positioned at the identified end of each of the primary structure and the primary structure table associates a primary structure and a cooccurrence rate of a certain amino acid combination positioned at an end of the primary structure, wherein the second identified primary structure has the highest co-occurrence rate among the primary structure candidates, using the processor;
    generating a primary structure compression file by compressing the protein file in units of primary structures based on the primary structure identified by the second identifying that is repeatedly performed and a primary structure dictionary associating a primary structure and a code with each other, the generated primary structure compression file including information in which a plurality of primary structure codes are arranged, using the processor; and
    generating a primary structure transposition index associating a primary structure type and a corresponding offset position in a sequence in the primary structure compression file with each other, using the processor.

2. A method of identification comprising:
    acquiring a codon file in which a plurality of codons are arranged, using a processor;
    first identifying a plurality of protein candidates with any position included in the codon file as a starting position, using the processor;
    second identifying one protein among the protein candidates based on a combination of each protein and a protein before the starting position and a protein table where each protein is included in the identified protein candidates and the protein table defines an appearance frequency of a protein following a certain protein in a protein identified by a codon sequence, using the processor;
    generating a protein compression file by compressing the codon file in units of proteins based on the protein identified by the second identifying and a protein dictionary associating a protein and a protein code with each other, the generated protein compression file including information in which a plurality of protein codes are arranged, using the processor; and
    generating a protein transposition index associating a protein type and a corresponding offset position in a sequence in the protein compression file with each other, using the processor.

3. The method of identification according to claim 2, further comprising generating the codon file by compressing a base file in units of codons based on a conversion table associating the base file including a base sequence and a codon code identified by a plurality of base sequences with each other.

4. The method of identification according to claim 3, further comprising generating a codon transposition index associating a codon type and a corresponding offset position in a sequence in the codon file with each other.

5. An identification apparatus comprising:
    a processor configured to:
    acquire a protein file in which a plurality of proteins including a plurality of amino acids are arranged;
    first identify a plurality of primary structure candidates with any position included in the protein file as a starting position, and identify an end of each of the primary structure candidates based on a primary structure dictionary index that indicates a position of a primary structure included in the protein file;
    second identify one primary structure among the primary structure candidates based on a combination of a primary structure and each amino acid and a primary structure table, where each amino acid is positioned at the identified end of each of the primary structure candidates and the primary structure table associates a primary structure and a cooccurrence rate of a certain amino acid combination positioned at an end of the primary structure, wherein the second identified primary structure has the highest cooccurrence rate among the primary structure candidates;

generate a primary structure compression file by compressing the protein file in units of primary structures based on the primary structure identified by the second identifying that is repeatedly performed and a primary structure dictionary associating a primary structure and a code with each other, the generated primary structure compression file including information in which a plurality of primary structure codes are arranged; and generate a primary structure transposition index associating a primary structure type and a corresponding offset position in a sequence in the primary structure compression file with each other.

6. An identification apparatus comprising:

a processor configured to:

acquire a codon file in which a plurality of codons are arranged;

first identify a plurality of protein candidates with any position included in the codon file as a starting position;

second identify one protein among the protein candidates based on a combination of each protein and a protein before the starting position and a protein table where each protein is included in the identified protein candidates and the protein table defines an appearance frequency of a protein following a certain protein in a protein identified by a codon sequence;

generate a protein compression file by compressing the codon file in units of proteins based on the protein identified by the second identifying and a protein dictionary associating a protein and a protein code with each other, the generated protein compression file including information in which a plurality of protein codes are arranged; and generate a protein transposition index associating a protein type and a corresponding offset position in a sequence in the protein compression file with each other.

7. The identification apparatus according to claim 6, wherein the processor is further configured to generate the codon file by compressing a base file in units of codons based on a conversion table associating the base file including a base sequence and a codon code identified by a plurality of base sequences with each other.

8. The identification apparatus according to claim 7, wherein the processor is further configured to generate a codon transposition index associating a codon type and a corresponding offset position in a sequence in the codon file with each other.

* * * * *